(12) United States Patent
Borenstein et al.

(10) Patent No.: US 11,628,437 B2
(45) Date of Patent: Apr. 18, 2023

(54) MICROFLUIDIC SYSTEM FOR EVALUATION OF CHEMOTHERAPEUTIC AND IMMUNOTHERAPEUTIC DRUGS

(71) Applicant: The Charles Stark Draper Laboratory, Inc., Cambridge, MA (US)

(72) Inventors: Jeffrey T. Borenstein, Newton, MA (US); Alla A. Gimbel, Medford, MA (US); Jose A. Santos, Westwood, MA (US); Daniel T. Doty, Arlington, MA (US); Nathan F. Moore, Providence, RI (US); Louis B. Kratchman, Quincy, MA (US); James Truslow, Boston, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 1175 days.

(21) Appl. No.: 15/942,052

(22) Filed: Mar. 30, 2018

(65) Prior Publication Data

US 2018/0280971 A1     Oct. 4, 2018

Related U.S. Application Data

(60) Provisional application No. 62/480,905, filed on Apr. 3, 2017.

(51) Int. Cl.
| | | |
|---|---|---|
| *B01L 3/00* | (2006.01) | |
| *C12Q 1/24* | (2006.01) | |
| *G01N 33/50* | (2006.01) | |

(52) U.S. Cl.
CPC ..... *B01L 3/50273* (2013.01); *B01L 3/502746* (2013.01); *B01L 3/502761* (2013.01); *C12Q 1/24* (2013.01); *G01N 33/5011* (2013.01); *B01L 2200/027* (2013.01); *B01L 2200/0647* (2013.01); *B01L 2300/0864* (2013.01); *B01L 2400/04* (2013.01); *B01L 2400/086* (2013.01)

(58) Field of Classification Search
CPC .......... B01L 3/50273; B01L 3/502746; B01L 2200/027; B01L 2400/04; B01L 3/502761; B01L 2200/0647; B01L 2400/086; C12Q 1/24
See application file for complete search history.

(56) References Cited

U.S. PATENT DOCUMENTS

| | | |
|---|---|---|
| 6,942,873 B2 | 9/2005 | Russell et al. |
| 2004/0005582 A1 | 1/2004 | Shipwash |
| 2006/0000772 A1 | 1/2006 | Sano et al. |
| 2006/0121624 A1 | 6/2006 | Huang et al. |
| 2009/0136982 A1 | 5/2009 | Tang et al. |
| 2010/0216241 A1 | 8/2010 | Yu et al. |
| 2011/0086427 A1 | 4/2011 | Faris et al. |
| 2011/0136162 A1 | 6/2011 | Sun et al. |
| 2011/0256574 A1 | 10/2011 | Zhang et al. |
| 2012/0329082 A1 | 12/2012 | Viola et al. |
| 2013/0005585 A1 | 1/2013 | Andersom et al. |
| 2014/0038279 A1 | 2/2014 | Ingber et al. |
| 2014/0127733 A1 | 5/2014 | Altiok et al. |
| 2016/0018365 A1 | 1/2016 | Agah et al. |
| 2016/0279637 A1 | 9/2016 | Sarioglu et al. |

FOREIGN PATENT DOCUMENTS

| | | | |
|---|---|---|---|
| EP | 0803288 A2 | 10/1997 | |
| WO | 2012050981 A1 | 4/2012 | |
| WO | WO-2012162779 A1 * | 12/2012 | ............... C12M 1/00 |
| WO | WO-2014039514 A2 * | 3/2014 | ................ B01J 4/00 |
| WO | 2016022722 A1 | 2/2016 | |

OTHER PUBLICATIONS

Schiavoni et al. The tumor microenvironment: a pitch for multiple players. Front. Oncol. 2013;3(90):1-15.*
Office Action dated Mar. 4, 2015 in U.S. Appl. No. 14/070,444.
Office Action dated Dec. 3, 2015 in U.S. Appl. No. 14/070,444.
International Search Report and Written Opinion dated Jan. 31, 2014 in PCT Application No. PCT/US2013/068168 (9 pages).
Office Action dated Jun. 21, 2017 in U.S. Appl. No. 14/586,577.
Notice of Allowance dated Oct. 12, 2017 in U.S. Appl. No. 14/586,577.
Doran, Marianne, Fine-Needle Aspiration Biopsy for Ocular and Orbital Tumors, Oncology, EyeNet, pp. 37-39, Jul. 2012.
Hattersley et al., A Microfludic System for Testing the Responses of Head and Neck Squamous Cell Carcinoma Tissue Biopsies to Treatment with Chemotherapy Drugs, Annals of Biomedical Engineering, vol. 40, No. 6, pp. 1277-1288 (Jun. 2012).
Prot et al, The Current Status of Alternative to Animal Testing and Predictive Toxicology Methods Using Liver Microfluidic Biochips, Annals of biomedical engineering, vol. 40, No. 6, pp. 1228-1243 (Jun. 2012).
Sorger, Peter K., Microfluidic closes in on point-of-care assays, Nature Biotechnology, vol. 26, No. 12, pp. 1345-1346 (Dec. 2008).
Vickerman et al., Design, fabrication and implementation of a novel multi-parameter control microfluidic platform for three-dimensional cell culture and real-time imaging, Lab on a Chip, vol. 8, No. 9, pp. 1468-1477 (Jul. 2008).
Zhang et al, Microfluidics and cancer: are we there yet?, Biomed Microdevices, vol. 15, No. 4, pp. 595-609 (Jan. 2013).

(Continued)

*Primary Examiner* — Lynn Y Fan
(74) *Attorney, Agent, or Firm* — McDermott Will & Emery

(57) ABSTRACT

Systems and methods for conducting assays on tissue fragment samples including providing a suspension maintaining pump, and a plurality of fluid reservoirs, wherein the fluid reservoirs are configured to hold a volume of fluid. The fluid reservoirs are fluidically coupled to a microfluidic assay chip, wherein the microfluidic assay chip includes a plurality of parallel assay channels, a first inlet port for introduction of a tissue fragment sample into the microfluidic assay ship, and a second inlet port coupled to the fluid reservoir. Each channel of the microfluidic assay chip also includes a retention barrier configured to trap the tissue fragment sample such that the fluid perfuses through the tissue sample, as well as an outlet port fluidically coupled to a waste receptacle.

12 Claims, 12 Drawing Sheets
(4 of 12 Drawing Sheet(s) Filed in Color)

(56) References Cited

OTHER PUBLICATIONS

FNBA. Procedures/diagnostic tests: interventional radiology. Clinical Center National Institutes of Health. 2010; 1-5.
Kim et al. In-situ synthesized and patterned nanowire arrays in microfluidic channel for particle trapping and cell lysis applications. 15th International Conference on Miniaturized Systems for Chemistry and Life Sciences. 2011; 1789-1791.
International Search Report and Written Opinion dated Jun. 6, 2018 in PCT Application No. PCT/US2018/025497.

\* cited by examiner

MICROFLUIDIC SYSTEM FOR EVALUATION OF CHEMOTHERAPEUTIC AND IMMUNOTHERAPEUTIC DRUGS

RELATED APPLICATIONS

The present application claims priority to, and the benefit of, U.S. Provisional Patent Application No. 62/480,905, entitled "MICROFLUIDIC SYSTEM FOR EVALUATION OF CHEMOTHERAPEUTIC AND IMMUNOTHERAPEUTIC DRUGS" and filed on Apr. 3, 2017, the entire contents of which are hereby incorporated by reference for all purposes.

BACKGROUND

Microfluidic devices have emerged as valuable tools for both mechanistic studies and for potential evaluation of therapeutic agents, due to their ability to precisely control drug concentrations gradients of oxygen, and other species in a scalable and potentially high throughput manner. The emergence of immune checkpoint inhibitors ("ICI") as a powerful therapeutic modality against many cancers has created a need for preclinical in vitro models that accommodate interactions between tumors and immune cells, particularly for assessment of unprocessed tumor fragments harvested directly from patient biopsies. The systems and methods described herein use a microfluidic assay chip that can accommodate a plurality of tumor samples interacting with circulating tumor infiltrating lymphocytes in a dynamic microenvironment. The systems and methods can also utilize a constant pump source, a pressure chamber, and a plurality of fluid reservoirs to control fluid flow through the microfluidic assay chip and tumor samples.

SUMMARY OF DISCLOSURE

According to one aspect, the disclosure relates to a system for conducting assays on tissue fragments. The system can include a suspension maintaining pump that includes a plurality of fluid reservoirs, wherein the fluid reservoirs are configured to hold a volume of fluid and solute suspended within the fluid. In some implementations, the solute contains tumor infiltrating lymphocytes. The system also includes a means for maintaining the solute in suspension within the fluid held in the fluid reservoirs. The system also includes a microfluidic assay chip, wherein the microfluidic assay chip includes a plurality of parallel assay channels. Each assay channel can include a first inlet at a proximal end of the channel for introduction of a tissue fragment into the microfluidic assay chip, and a second inlet at the proximal end of the channel coupling a fluid reservoir to a respective assay channel, wherein the coupling comprises a portion of the tubing. In some implementations, the tissue fragment comprises portions of animal or human tumors or engineered tumor spheroids. The system also includes a retention barrier located within the assay channel configured to trap a tissue fragment sample such that the fluid and solute perfuses through the tissue fragment sample. In some implementations, the retention barrier comprises a plurality of posts extending from the bottom of the channel to the top of the channel.

The system also includes an outlet at the distal end of the channel, which allows fluid and solute to flow out of the microfluidic assay chip. In some implementations, the system includes resistive tubing to route fluid from the outlet of each assay channel to a waste receptacle. In other implementations, the resistive tubing can route fluid from the outlet of each assay channel to a recirculating pump for pumping fluid flowed through the microfluidic assay chip back to respective fluid reservoirs. The system also includes tubing fluidically coupling the suspension maintaining pump to the first inlets of the assay channels of the microfluidic assay chip.

In some implementations, the suspension maintaining pump includes a stirred syringe pump, a stirred peristaltic pump, or a constant pressure pump. In some implementations, the suspension maintaining pump is configured to apply a constant pressure to the fluid in the fluid reservoirs.

In some implementations, the system also includes a plurality of bubble traps located between the fluid reservoirs and the microfluidic assay chip, each bubble trap having an exit port located below an entry port configured to remove gas bubbles from the fluid. In some implementations, the exit ports of the bubble traps comprise a conical shape configured to funnel media and cells out of the bubble trap. In some implementations, the system also includes a plurality of particulate traps located between the microfluidic assay chip and a waste receptacle, each particulate trap having an exit port located above the entry port and being configured to remove cells from the fluid exiting the microfluidic assay chip before entering the resistive tubing.

In some implementations, the suspension maintaining means includes a stirrer rod for each fluid reservoir and a magnetic or electromagnetic plate configured to oscillate, wherein the oscillation causes motion of the respective stirrer rods, thereby stirring the fluid within the reservoirs. In some implementations, the system includes an imaging device for optically monitoring a state of the tissue fragment sample located within the retention barrier.

According to one aspect, the disclosure relates to a method of evaluating the efficacy of agents on tissue fragments. The method includes providing a suspension maintaining pump including a means for maintaining suspension of a solute in the fluid, and a plurality of fluid reservoirs, wherein the fluid reservoirs are configured to hold a volume of fluid and solute suspended within the fluid fluidically coupled to a microfluidic assay chip by tubing. The microfluidic assay chip includes a plurality of parallel assay channels. Each microfluidic assay channel includes a first inlet at a proximal end of the channel for introduction of a tissue fragment into the microfluidic assay chip, a second inlet at the proximal end of the channel coupling a fluid reservoir to a respective assay channel, wherein the coupling comprises a portion of the tubing, a retention barrier located within the assay channel and configured to trap a tissue fragment sample such that the fluid and solute perfuses through the tissue fragment sample, and an outlet at the distal end of the channel configured to allow fluid and solute to flow out of the microfluidic assay chip. In some implementations, the tissue fragment includes portions of animal or human tumors or engineered tumor spheroids. In some implementations, the tumor is between 75 and 500 microns in diameter. The method also includes introducing the tissue fragment samples to the array of parallel assay channels via the set of first inlets. The method also includes retaining the tissue fragment samples in the respective channels via respective retention barriers and flowing fluid from the fluid reservoirs located in the constant pressure pump into the proximal ends of the respective assay channels via the respective second inlets such that the fluid and solute flows through the respective channels, thereby inducing interstitial flow of the fluid and solute through the tissue fragment samples such that the fluid and solute perfuses through the tissue fragment samples. In some implementations, the fluid in at least one of the fluid reservoirs contains tumor infiltrating lymphocytes. In some implementations, the retention barrier comprises a plurality of posts extending from the bottom of the channel to the top of the channel. The method also includes collecting the fluid and solute at the outlet at a distal end of the channel and monitoring the condition of the tissue fragment samples over time during the flowing of the fluid and solute.

In some implementations, the suspension maintaining pump includes a stirred syringe pump, a stirred peristaltic pump, or a constant pressure pump. In some implementations, the suspension maintaining pump comprises a constant pressure source.

In some implementations, the method further includes removing bubbles from the fluid prior to its introduction into the respective assay channels with a plurality of bubble traps located between the fluid reservoirs and the microfluidic assay chip, each bubble trap having an exit port located below an entry port configured to remove gas bubbles from the fluid.

In some implementations, the method can include routing the fluid through the resistive tubing from the outlet of each assay channel to a waste receptacle. In other implementations, the method can include routing the fluid through the resistive tubing from the outlet of each assay channel to a recirculating pump for pumping fluid flowed through the microfluidic assay chip back to respective reservoirs. In some implementations, the method includes removing cells from the fluid before the fluid enters the waste receptacle with a plurality of particulate traps located between the microfluidic assay chip and the waste receptacle.

In some implementations, the suspension maintaining means is configured to stir the fluid in each fluid reservoir with a stirrer rod and a magnetic or electromagnetic plate configured to oscillate, wherein the oscillation of the plate causes motion of the respective stirrer rods within the reservoirs, thereby maintaining suspension of the solutes in the fluid within the reservoirs. In some implementations, the method can include monitoring the tissue fragment sample located within the retention barrier with an imaging device.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example implementations of the invention, as illustrated in the accompanying drawings. The drawings are not necessarily to scale, emphasis instead being placed upon illustrating implementations of the present invention.

For purposes of clarity, not every component may be labeled in every figure. The drawings are not intended to be drawn to scale. Like reference numbers and designations in the various figures indicate like elements.

DETAILED DESCRIPTION

Figure 1:
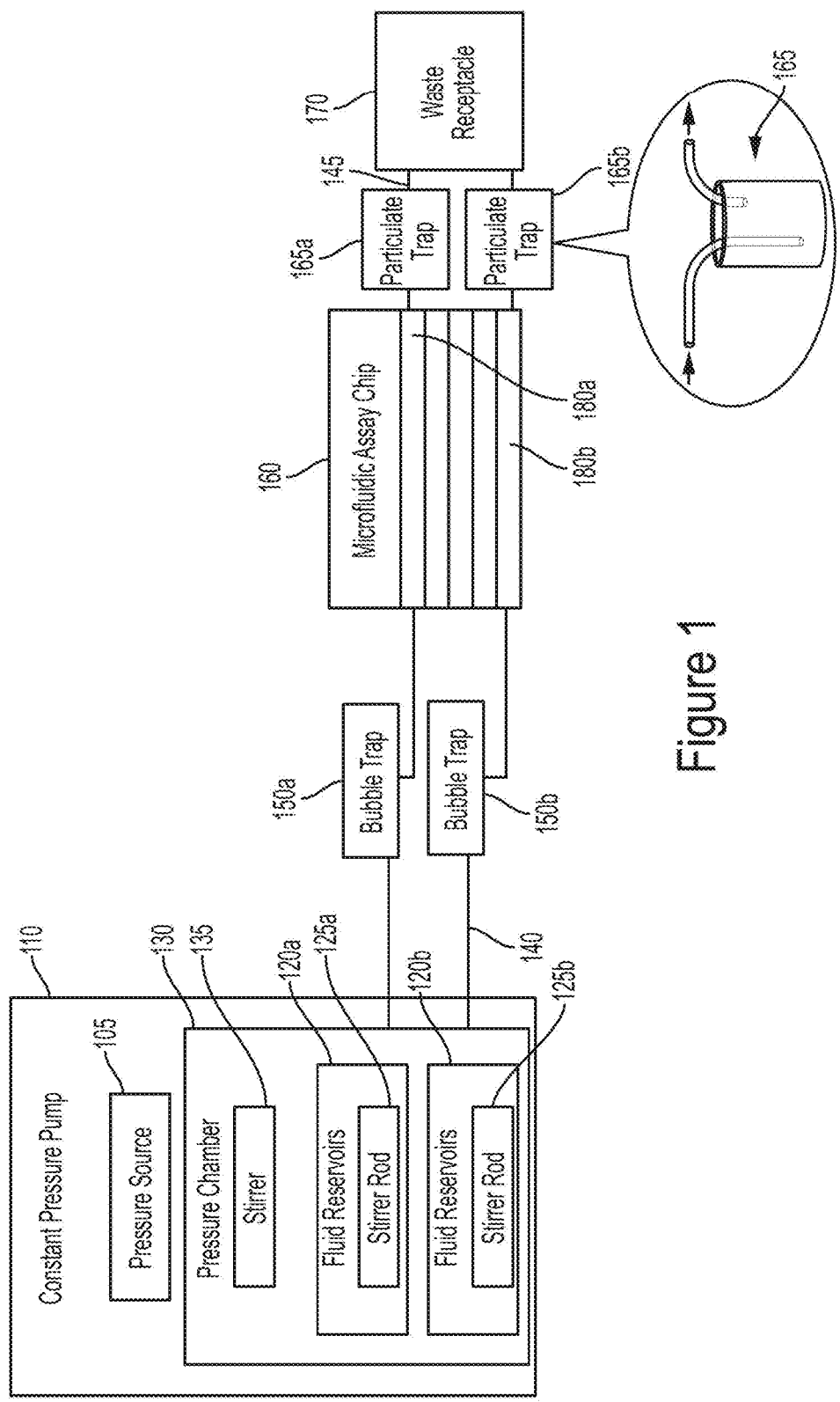
FIG. 1 shows a schematic diagram of a first example system for conducting assays on tumor samples.

Cells of the immune system are particularly important in the context of tumor therapy. Immunotherapeutic strategies permit selective killing of tumor cells while minimizing many of the side effects associated with traditional chemotherapy. Moreover, immune cells can be manipulated to specifically recognize cancer cells and target them for destruction prior to the onset of events such as metastasis. One form of immunotherapy makes use of autologous immune cells to destroy tumors. This technique—termed adoptive cell transfer ("ACT")—primarily relies on the anti-tumor activity of tumor infiltrating lymphocytes ("TIL") or genetically re-directed peripheral blood mononuclear cells to treat a variety of cancers, including, solid tumors such as melanoma and colorectal carcinoma, cervical cancer, lung cancer, breast cancer, sarcoma, neuroblastoma, melanoma, hematologic malignancies such as lymphoma, leukemia, including refractory and/or relapsed forms thereof, etc.

Although ACT therapeutic methods carry much promise, there are numerous challenges that limit largescale implementation of the technology in the clinical setting. For instance, because primary cells are susceptible to mechanical stress and/or undergo apoptosis outside the host system, only a small percentage of isolated immune cells can be utilized for treatment. Additionally, extrinsic factors such as difficulties associated with the isolation, manipulation, expansion, and delivery of immune cells may also add to the complexity and to the overall cost of implementing the technology. Among the aforementioned drawbacks. one issue is the lack of appropriate model systems to test TIL activity.

To address these challenges, a variety of model systems have been developed. Traditional in vitro systems mainly utilize static 2D systems (e.g., cell culture plates) or 3D systems (e.g., mesh or fibrous surfaces). While such systems are important to the development of biologicals, they fail to mimic the tumor microenvironment. In contrast to linear 2D systems or uniform 3D systems, solid tumors are surrounded by membranes, fibrous layers, adhesion proteins, neighboring cells, tissues, etc. Additionally, the tumor microenvironment is inflammatory and dynamic and static in vitro systems do not adequately mimic the tumors because they fail to account for the paracrine, intracrine and/or endocrine signaling between different cells and tissues within a tumor. Additionally, isolated immune cells cannot be tested in the same breadth as small molecule compounds and/or biologicals because they are subject specific. For instance, there are few reliable in vitro and/or pre-clinical models to test autologous immune cells.

The systems and methods described herein are used to address the aforementioned concerns. For instance, the disclosed systems and methods better mimic in vivo conditions and permit screening and testing of labile candidates. For instance, the systems disclosed herein can be used to rapidly study the susceptibility of a tumor specimen against both biological agents, such as TILs, as well as small molecule compounds by using a constant pressure pump, fluid reservoirs, and a microfluidic assay chip. The microfluidic assay chip includes a plurality of channels to retain tumor samples. The constant pressure pump perfuses fluid through the tumor samples from the fluid reservoirs in the constant pressure pump. In some implementations, the system and methods also includes bubble traps, receptacles, and resistive tubing that couples the microfluidic pump source to the waste receptacles. In some implementations, the system and methods may include a recirculating pump.

To provide an overall understanding of the invention, certain illustrative implementations will now be described, including the constant pressure pump and microfluidic assay chip for culturing cells in a biomimetic environment. However, it will be understood by one of ordinary skill in the art that the systems and methods described herein may be adapted and modified as is appropriate for the application being addressed and that the systems and methods described herein may be employed in other suitable applications, and that such other additions and modifications will not depart from the scope thereof. The various concepts introduced above and discussed in greater detail below may be implemented in any of numerous ways, as the described concepts are not limited to any particular manner of implementation. Examples of specific implementations and applications are provided primarily for illustrative purposes.

FIG. 1 shows a schematic diagram of a first example system for conducting assays on tumor samples. The system includes a constant pressure pump 110, a pressure source 105, a microfluidic assay chip 160, a plurality of reservoirs 120a and 120b (generally referred to as reservoirs 120), a pressure chamber 130, bubble traps 150a and 150b (generally referred to as bubble traps 150), particulate traps 165a and 165b (generally referred to as particulate traps 165), and a waste receptacle 170. The microfluidic chip 160 includes multiple tumor assay channels 180a and 180b (generally referred to as tumor assay channels 180) arranged in parallel and described further below in FIG. 3. The constant pressure pump 110 fluidically couples to each tumor assay channel 180 via tubing 140 and the bubble traps 150, an example of which is discussed further in relation to FIG. 5 below. The distal end of the microfluidic assay chip 160 is fluidically coupled to the waste receptacle 170 via the particulate traps 165 and resistive tubing 145.

The plurality of particulate traps 165 function to remove cells after introduction to a tumor sample or other tissue fragment in the microfluidic assay chip 160, wherein each tumor assay channel is coupled to a respective particulate trap 165. The particulate traps 165 can be pressurized vessels filled with fluid, e.g., media or phosphate-buffered saline ("PBS"), and capped with a septa or other fitting that allows for the tubing to pass through but remain airtight. Fluid containing TILs and potential debris from the tumor or other tissue fragment present within each tumor assay channel 180 flows in from the microfluidic assay chip 160, through the septa, to be deposited at the bottom of each respective particulate trap 165. Gravity causes TILs and tumor fragments to sink and remain near the bottom of the particulate trap 165. Pressure introduced into the particulate trap 165 from the fluidic flow drives the remaining fluid out of the top of the particulate trap 165, through the resistance tubing 145 and into the waste receptacle 170. The particulate traps 165 prevent TILs and tumor fragments flowing downstream of the microfluidic assay chip 165 from moving through the small bore of the resistance tubing 145 and potentially clogging the fluidic pathway. Additionally, the particulate traps 165 allow for collection of TILs that have passed through each individual channel of the device. In some implementations, the particulate traps 165 function to remove cells from the fluid in order to reuse them in the same experiment, or in some implementations, the particulate traps 165 remove the cells to reuse them in different experiments to study their effectiveness on a different tumor sample or tissue fragment. The collection of TILs in each respective particulate trap 165 also enables recirculation, counting, and downstream analysis of the captured TILs, such as an analysis of activation markers or measurements of the release of interferon gamma.

As mentioned above the system shown in FIG. 1 also includes a constant pressure pump 110 and a pressure source 105. The pressure source 105 applies precise levels of applied pressure, balanced against the hydraulic resistance of the flow circuit, to drive the fluid through the tubing that couples the microfluidic assay chip 160. In some implementations, the pressure source may be a compressed gas cylinder, wherein compressed air and 5% $CO_2$ are applied to the system. In some implementations, other custom gases may be used for experiments to more closely mimic the oxygen and $CO_2$ levels within the microenvironment of specific tumor types. The constant pressure pump 110 includes one or more pressure chambers(s) 130, a pump source 105, and a plurality of reservoirs 120. In some implementations, the reservoirs 120 are located in one or more physically separated housings than the pressure chambers (s) 130. In some implementations, some or all of the reservoirs 120 are located in the same physical housing as the pressure chambers (s) 130. In some implementations, for example, assays in which each tumor assay channel 180 is to receive a different fluid (or a fluid carrying different potential treatments), the constant pressure pump 110 can includes one reservoir for each tumor assay channel 180 in the microfluidic assay chip 160. For example, in FIG. 1 fluid reservoir 120a connects to the bubble trap 150a and microfluidic channel 180a. Similarly, fluid reservoir 120b connects to the bubble trap 150b and microfluidic channel 180b. In some other implementations, for example in which multiple tumor assay channels 180 are to receive the same fluid, the constant pressure pump 110 can include fewer reservoirs 120 (as few as one if all channels are to receive the same fluid) than there are tumor assay channels 180 in the microfluidic assay chip 160. The reservoirs 120 in the system of FIG. 1 are large enough to store enough fluid to conduct the desired experiment, without fluid recirculation. In some implementations, a stirrer 135 or other agitator are coupled to stirring rods 125a and 125b, generally referred to as stirring rods 125, within the reservoirs 120 to maintain the distribution of agents (e.g., small molecules, large molecules, lymphocytes, etc.) in suspension in the media filling the reservoirs 120.

Is some implementations, the pressure chambers 130 generates a fluidic pressure on a side of a membrane, and the reservoirs 120 are located on the other side of the membrane. Application of pressure on the membrane distends the membrane, causing fluid to flow out of the reservoirs 120 into the tubing 140 towards the microfluidic assay chip 160. As such, in some implementations, one pressure chamber 130 can distribute fluid from multiple reservoirs 120 simultaneously. In some implementations, a check valve can be placed between the reservoirs 120 and the tubing 140 to avoid back-flow when the pressure on the membrane is relieved during a pump cycle. In some other implementations, each reservoir 120 forms an isolated fluidic column in the pressure chamber 130. In such implementations, the pressure chambers 130 forces air or an inert gas into the pressure chamber 130 at a constant rate, forcing out the fluid in the reservoirs 120 as more gas is introduced into the pressure chamber 130. The partial pressure of each gas that is exposed to the cells within the pressure chamber 130 can be precisely controlled. In some implementations, the entire system is closed, and all components are gas impermeable; therefore, the only gasses introduced into the system are pumped into the pressure chamber 130 and supplied by the pressure source 105. In some implementations, the gasses may be compressed air with an added 5% $CO_2$. In some implementations, the gases may represent a hypoxic condition. In some implementations, the gases may closely mimic the oxygen and $CO_2$ levels within the microenvironment of specific tumor types.

As mentioned above the system shown in FIG. 1 includes a constant pressure pump 110. More generally, the pump 110 in FIG. 1 can be any form of suspension maintaining pump. A constant pressure pump with a magnetic stirrer is one example of such a suspension maintaining pump. As used herein, a suspension maintaining pump is a pump is configured to maintain solutes in suspension with a fluid stored within the pump. In the context of the system shown in FIG. 1, the suspension maintaining pump acts to keep cells, TILs, or other solid (generally a solute) disposed within the fluid to be pumped through the system suspended and evenly distributed in the fluid without causing damage to the solute's integrity. In some implementations, the suspension maintaining pump includes a stirred syringe pump, a stirred peristaltic pump, a hydraulic pump, or a constant pressure pump. For each of these implementations, the suspension of the solute may be maintained by rocking, shaking, or agitating a fluid reservoir included in the pump or stirring, or agitating the fluid within the fluid reservoirs, e.g., with magnetic stirrers with associated magnetic actuators (such as oscillating magnetic or electromagnetic plates), mechanical stirring rods, rockers, bubblers, acoustic agitators, or other mixing or agitation elements. In some implementations, the suspension of the solute may be maintained by stirring or mixing the fluid in the fluid reservoirs with chaotic mixers or other passive fluid elements. In some implementations, the means for maintaining suspension of the solute may be external to the fluid reservoir, internal to the fluid reservoir, a partially internal and partially external to the fluid reservoir. For example, a magnetic stirrer rod or other magnetic stirring element can be placed within the fluid reservoirs and a corresponding magnet or electromagnet that drives the magnetic stirrer can be external to the fluid reservoir.

For the sake of brevity, the remainder of this disclosure describes systems that include a constant pressure pump. However, it is to be understood that each other implementation disclosed herein may also be implemented using any of the alternative suspension maintaining pump architectures referenced above.

Figure 2:
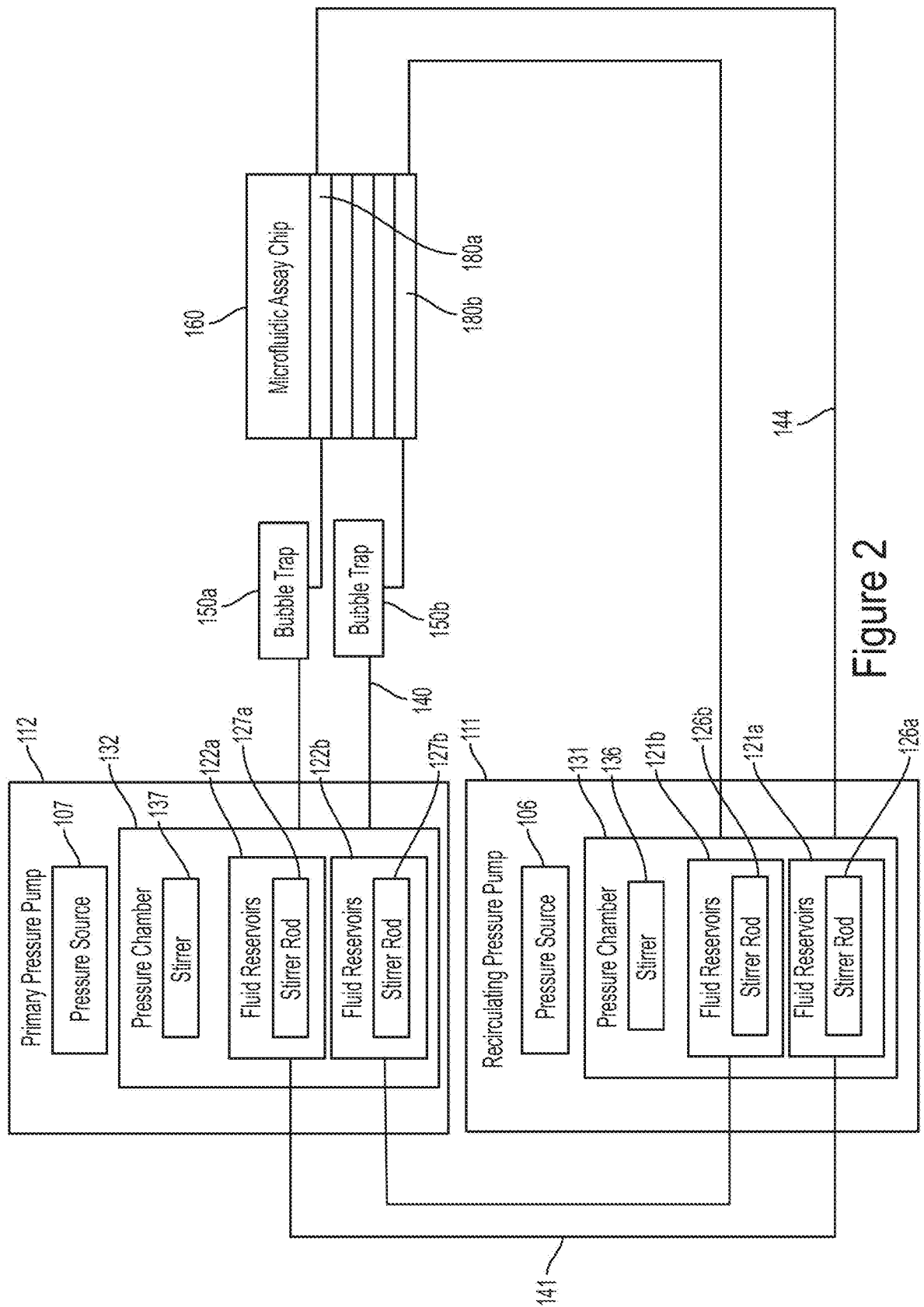
FIG. 2 shows a schematic diagram of a second example system for conducting assays on tumor samples.

FIG. 2 shows a schematic diagram of a second example system 200 for conducting assays on tumor samples. The system shown in FIG. 2 is similar to that shown in FIG. 1, except for it introduces a recirculating pressure pump 111, to provide for recirculating flow through the system in addition to a primary pressure pump 112.

The recirculating pressure pump 111 includes one or more pressure chambers 131 and a plurality of reservoirs 121a and 121b, generally referred to as reservoirs 121. The recirculating pressure pump 111 can have the same number of reservoirs 121 as the primary pressure pump 112. In some implementations, the primary pressure pump 112 can have more or less reservoirs as the recirculating pressure pump 111. FIG. 2 also includes a microfluidic assay chip 160 and a plurality of tumor assay channels 180a and 180b, generally referred to as assay channels 180. The distal end of each assay channel 180a and 180b is coupled to a respective fluid reservoir 121a and 121b in the recirculating pressure pump 111 by resistive tubing 144. Each fluid reservoir 121 in the recirculating pressure pump 111 is fluidically coupled by tubing 141 back to the fluid reservoirs 122a and 122b, respectively, which served as the original source of fluid in the primary pressure pump 112 within a pressure chamber 132. The tubing 141 coupling the recirculating pressure pump 111 to the primary pressure pump fluid reservoirs 122 can have a larger inner diameter than the tubing 140 leading away from the fluid reservoirs 122, thereby allowing for a higher flow rate back to the primary pump reservoirs 122, without increasing the shear on the fluid flowing through the tubing 141. Similar to FIG. 1, FIG. 2 also includes a plurality of bubble traps 150a and 150b, collectively 150 coupled to respective channels 180a and 180b of the microfluidic assay chip. The bubbles traps 150 and the pressure sources 106 and 107 function similarly to the bubbles traps 150 and pressure source 105 described in FIG. 1 above and FIGS. 5A and 5B below. FIG. 2 also includes a pressure source 107 located in the primary pressure pump and a pressure source 106 located in the recirculating pressure pump 111. The primary pressure pump 112 also includes a stirrer 137 and a plurality of stirrer rods 127a and 127b, generally referred to as stirrer rods 127. The recirculating pressure pump 111 also includes a stirrer 136 and a plurality of stirrer rods 126a and 126b, generally referred to as stirrer rods 126.

In order to provide a pressure drop from the reservoirs in the primary pressure pump 112 to the recirculating pressure pump 111, in some implementations, the fluid reservoirs 121 in the recirculating pressure pump 111 may be maintained at the ambient pressure.

In operation, in some implementations, both pressure pumps 112 and 111 can operate at the same time, though in some cases they are out of phase, thus maintaining a continuous recirculating flow. In some other implementations, the recirculating pressure pump 111 operates in a batch pumping manner, in which the recirculating pump fluid reservoirs 121 are initially empty and fill with fluid pumped by the primary pressure pump 112. After a predetermined amount of fluid has reached the recirculating pump fluid reservoirs 121, or a predetermined amount of time has passed, the primary pressure pump 112 temporarily ceases operation, while the recirculating pressure pump 111 pumps the fluid in its reservoirs 121 back to the primary pressure pump fluid reservoirs 122.

In some implementations, the fluid in the fluid reservoirs 120 may contain tumor infiltrating lymphocytes ("TILs"). The TIL populations that may be tested or screened include, but are not limited to, B cells, T cells, cytotoxic T cells, helper T cells, regulatory T cells, Th1 T helper cells, TH2 T helper cells, TH9 helper T cells, Th17 helper T cells, Tfh helper T cells, antigen-specific T cells, and antigen-specific B cells. In some implementations, the systems and methods using TIL-mediated tumor killing and TIL infiltration may be achieved by harvesting mouse or human tumors, separating them into sister fragments, digesting some samples and harvesting and potentially expanding resident TIL populations, and then dynamically interacting the harvested TILs with remaining fragments. Digested TILs may be reintroduced into the microfluidic system in an unmodified form, or may be treated with small molecules, immune checkpoint inhibitors ("ICI"), or combination therapies prior to reintroduction in order to assess the efficacy of various drug therapies against specific tumor types or patient samples.

For some implementations of the systems shown in FIGS. 1 and 2, flow sensors (not shown) are incorporated along the flow path between the primary constant pressure pump 110 and the microfluidic assay chip 160, or between the microfluidic assay chip 160 and the waste receptacle 170 or the recirculating pump 111. In other implementations, particularly implementations used for conducting tumor assays involving TILs, the fluid sensors are omitted as it has been found that TILs are particularly sensitive to physical disruption, and can be damaged or destroyed by flowing through or over flow sensors. Omitting flow sensors in such systems therefore helps maintain TIL integrity. Instead, flow rates are governed based on flow rate measurements obtained from empirical testing of the device at various pump pressures, prior to introduction of TILs. In some implementations, the flow pressure is between about 80-100 mbar, providing about 1.0-1.5 µl/min of flow through each tumor assay channel.

In some implementations, the systems and methods described herein can be used to study the susceptibility of a tumor specimen against both biological agents as well as small molecule compounds. For instance, the susceptibility of a solid tumor derived cell line towards a small molecule such as staurosporine or a larger molecule such as an anti-PD-1 antibody and cells such as TILs can be studied in real time. In some implementations, the system and methods described herein can be further utilized to identify new druggable targets, e.g., identify tumors that are susceptible to a particular class of drugs, which may lead to novel insights about particular therapeutics modalities of the drugs. Additionally, the systems and methods disclosed may serve as an improved system for screening new anticancer compounds and other drugs of interest. In some implementations, other system components can be added to the systems shown in FIGS. 1 and 2, such as confocal microscopes for observing the state of tumor samples trapped in retention barriers. Some such implementations can include digital cameras coupled to a computer executing automated monitoring software, such as cell counting software or fluorescence monitoring software. A display can output the results of the monitoring in real-time and/or upon operator request or instruction. The computer can further be configured for controlling the pump(s), for example to coordinate activity of the primary and recirculating pumps of the system shown in FIG. 2.

Figure 3A:
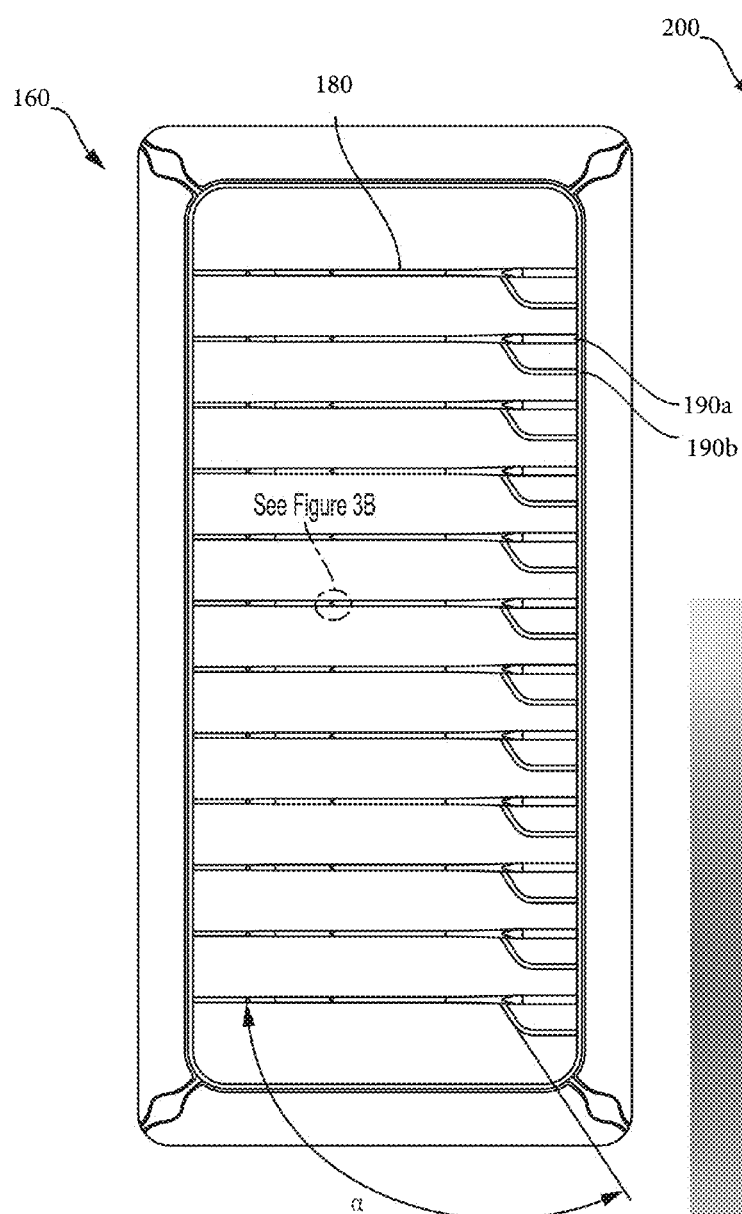
FIG. 3A shows a schematic diagram of an example microfluidic chip suitable for use in the systems of FIGS. 1 and 2.
Figure 3B:
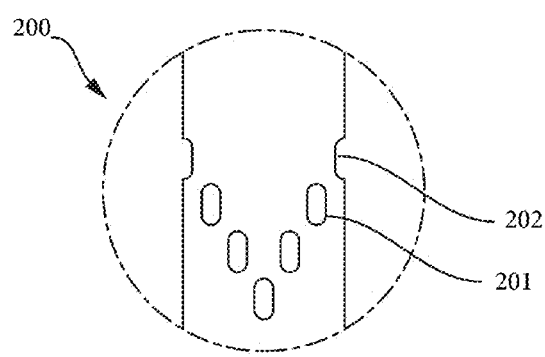
FIG. 3B shows an example retention barrier within the tumor assay channel.
Figure 3C:
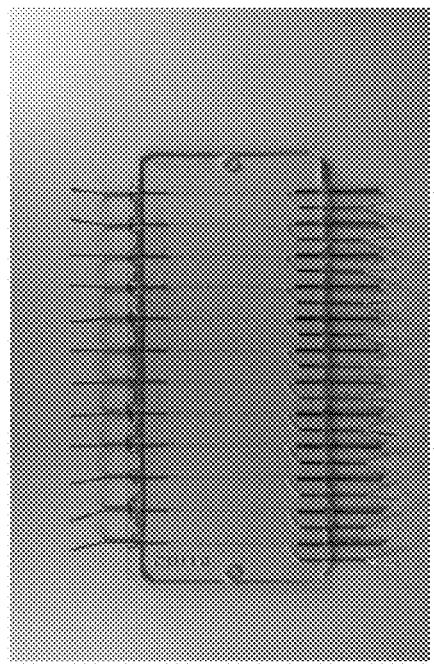
FIG. 3C shows a photograph of an example microfluidic chip suitable for use in the systems of FIGS. 1 and 2.

FIGS. 3A-3C show examples of a microfluidic assay chip and a retention barrier. FIG. 3A shows a schematic illustration of an example microfluidic assay chip 160 suitable for use in the systems of FIGS. 1 and 2. In general, the microfluidic assay chip 160 includes multiple tumor assay channels 180 arranged in parallel. Each channel has two inlet ports 190a and 190b, collectively the inlets 190. The first inlet 190a is aligned with the primary length of the channel 180 and is sized to receive a tumor sample, for example, via a syringe. The second inlet 190b is located besides the first inlet 190a and connects to the tumor assay channel 180 along its length at an angle, a. Referring to FIGS. 1 and 2, the fluidic connections from the constant pump source 110, through the bubble traps 150, connect to the tumor assay channels 180 through respective ones of these second inlets 190b. The tumor assay channels 180 each include a retention barrier 200, as shown in FIG. 3B, for trapping tumor samples introduced through the first inlets 190a, discussed further below.

In FIG. 3A, the channel connecting each second inlet 190b to the primary length of its corresponding tumor assay channel 180 connects to the tumor assay channel 180 at an angle of about 120°, shown in FIG. 3A as α. In various implementations, this angle can range from about 110°-130°. The retention barriers 200 can be located between abut 12-18 mm (e.g., about 15 mm) downstream from the junction where fluid introduced into the second inlet 190b enters the primary length of the tumor assay channel 180. The first inlet 190a can have a diameter of about 0.75-0.80 mm at its proximal end, whereas the second inlet 190b can have a diameter of between about 0.40 mm-0.60 mm (e.g., about 0.5 mm). The channel connecting the second inlet 190b to the primary length of the tumor assay channel 180 may include a bend or curve. This bend or curve can have a radius of curvature of between about 1.5 mm-2.0 mm. In some implementations, the entire tumor assay channel may be between about 20 mm-50 mm long. While the exact dimensions can vary in various implementations, the dimensions and geometric parameters shown in the figure and set forth above have been found to limit mechanical stresses on TILs flowing through the microfluidic assay chip, helping preserve the integrity of the TILs. FIG. 3C shows a photograph of an example microfluidic assay chip with metal first inlet ports 190a and metal second inlet ports 190b for receiving either the tubing 140 for fluid flow or a syringe for tumor introduction.

In some implementations, the walls of the tumor assay channel may be functionalized with one or more materials. Suitable materials include, without limitation, fibrinogen, Pluronic F127 and PEG (PolyEthylene Glycol). In some implementations, the channels may have rectangular or trapezoidal cross sections. In other implementations, the channels may have rounded or even circular cross sections. The channels in some implementations are closed at the top, and in other implementations, the channels are open in other implementations.

In some implementations, the microfluidic assay chip 160 can be formed primarily from a low autofluorescence, high transparency material, such as Cyclic Olefin Copolymer (COC). In other implementations, the microfluidic assay chip 160 may be formed from another hard plastic, glass or PDMS. The inlets 190 may include biocompatible metal inserts that serve as ports for receiving either the tubing 140 for fluid flow or a syringe for tumor introduction.

While the microfluidic assay chips shown in FIG. 3A has twelve tumor assay channels, in other implementations, the microfluidic assay chips can include fewer or additional tumor assay channels without departing from the scope of the invention.

FIG. 3B shows an example retention barrier 200 within a tumor assay channel 180. In some implementations of the microfluidic assay chip 160, the retention barrier 200 is formed form a series of posts arranged in a chevron like pattern across the width of the channel to trap tumor samples in the center while allowing for media and TIL flow around and over the tumor fragments. In some other implementations, the retention barrier 200 can take other forms, such as a vertical screen, a mesh, a gel, a cross hatch, a partial wall, posts in alternate arrangements (e.g., in a U shape or a straight line of vertical posts), or other form suitable for preventing a tumor to pass through, while still allowing fluid to flow through the channel and to mimic flow through the tumor sample similar to that experienced in in-vivo conditions. In FIG. 3B, the example retention barrier 200 is formed from five standalone posts, collectively 201 and two wall-protruding posts, collectively 202. One particular challenge with conducting assays using TILs is the extreme sensitivity to mechanical damage from anomalous flow patterns and device features that TILs tend to exhibit. As such, devices for testing TIL efficacy are designed to limit such flow patterns, maintain shear levels within acceptable limits, and avoid TIL contact with potentially damaging physical device features.

Figure 4A:
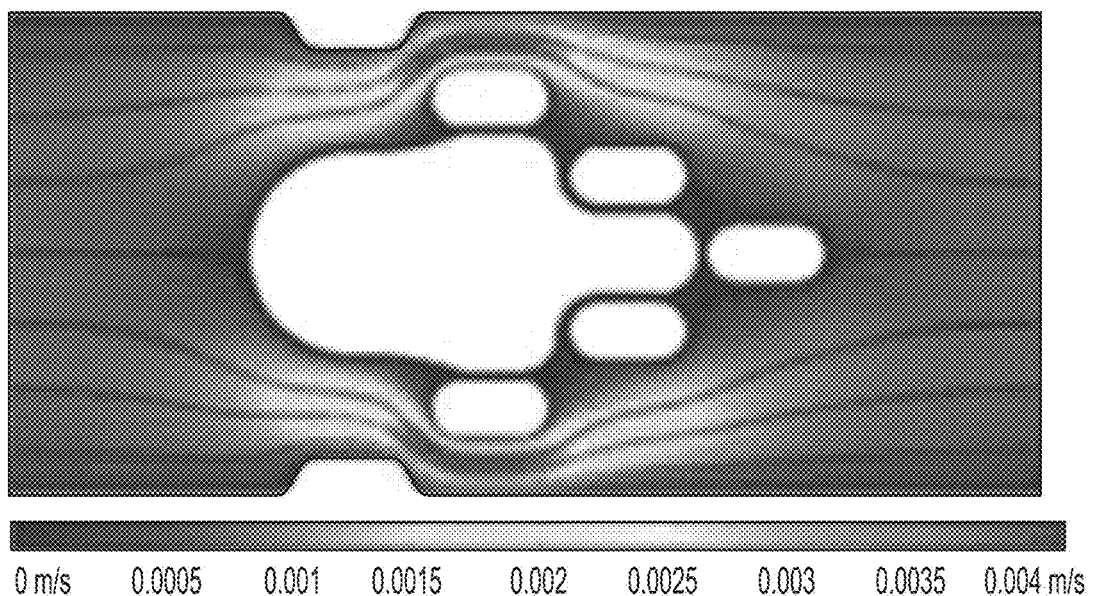
FIG. 4A illustrates the flow modeling of the example tumor retention barrier from FIG. 3B
Figure 4B:
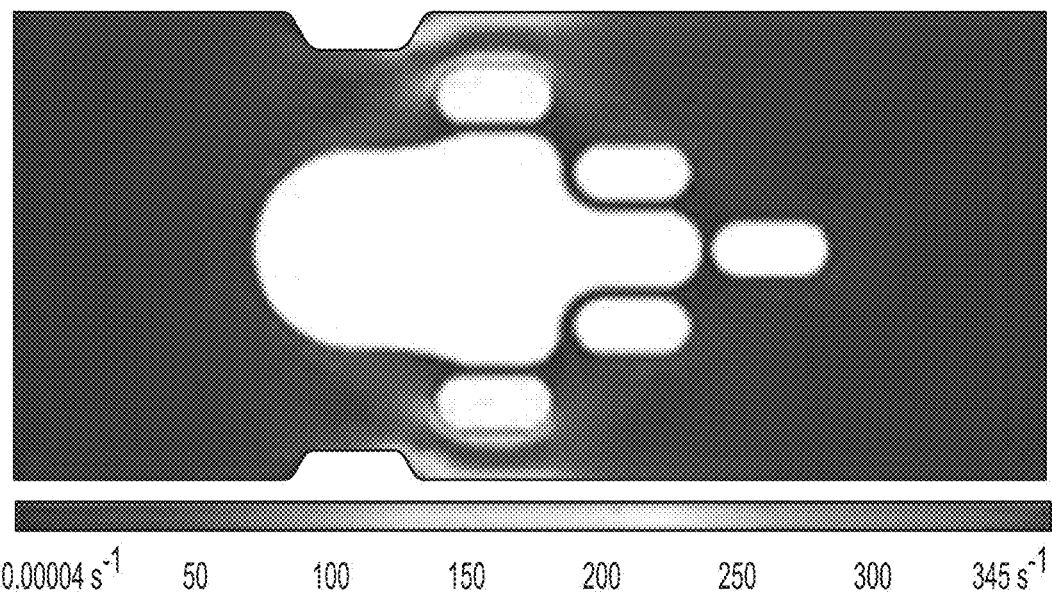
FIG. 4B illustrates the shear modeling of the example tumor retention barrier from FIG. 3B.

FIGS. 4A and 4B show examples of flow and shear distributions for the post pattern of FIG. 3B that was fabricated with a fluid flow rate of 1 µL/min, given a nominal tumor shape. FIG. 4A illustrates the flow modeling of the example tumor retention barrier 200 from FIG. 3B, which shows how the wall-protruding posts 202 help direct flow, including molecules or cells suspended in the flow, inwards towards a tumor trapped in the retention barrier 200, limiting the amount of flow that can fully bypass the tumor, which ensures that the tumor sample is infiltrated with the TIL fluid rather than shredded between the posts. FIG. 4B illustrates the shear modeling of the example tumor retention barrier 200 from FIG. 3B. Similar to FIG. 4A, the wall-protruding posts 202 help direct flow, including molecules or cells suspended in the flow, inwards towards the tumor trapped in the retention barrier 200, so that TILs in the flow stream cannot easily avoid striking the tissue sample as they pass by. Precise control over the flow rate enables the system to achieve a balance between adequate perfusion of the tissue sample to maintain viability and a sufficiently low shear stress to avoid shear damage. A lower shear helps avoid damage to TILs as they flow through the device, and helps protect the tissue fragment from shear damage as well. In addition, given the relative narrow lateral distance between posts, for example between about 0.025 mm-0.05 mm, fabricating standalone posts 201 that close to the wall poses substantial challenges. Having the posts closest to wall connect to and protrude out from the wall obviates this fabrication challenge. Each post can be about 0.075 mm-0.125 mm high and about 0.05 mm-0.10 mm wide. The post pattern is designed to trap tumor fragments with a size range of interest and to accept variations in fragment size and shape without permitting fragments to slip through the posts or to be shredded by excessive flow through the gaps between the posts. In a twelve channel microfluidic assay chip, each channel can measure about 25 mm long by 600 µm wide and 125 µm deep. The height of the channel is chosen to accommodate tumor fragments while balancing perfusion through and around the tumor fragment.

In some implementations, other protrusions can extend outward from the wall upstream of the retention barrier to direct fluid borne particles, such as TILs, inward towards the center of the channel to increase the likelihood of their interaction with a tumor trapped in the retention barrier 200. Other structures may extend upwards from, or into, the floor of the tumor assay channel 180 upstream from the retention barrier 200 to introduce limited amounts of turbulence and mixing to help reduce the likelihood of particle clumping or adherence to the walls of the tumor assay channel.

Figure 5B:
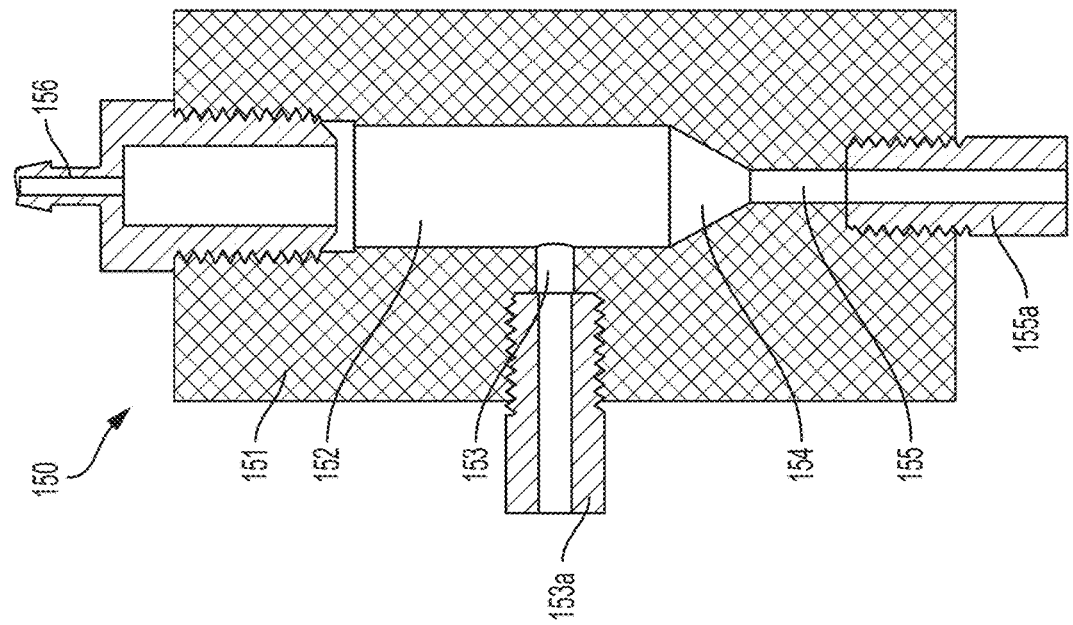
FIG. 5B shows a cross-sectional view of the example bubble trap shown in FIG. 5A and suitable for use in the systems shown in FIGS. 1 and 2.
Figure 5A:
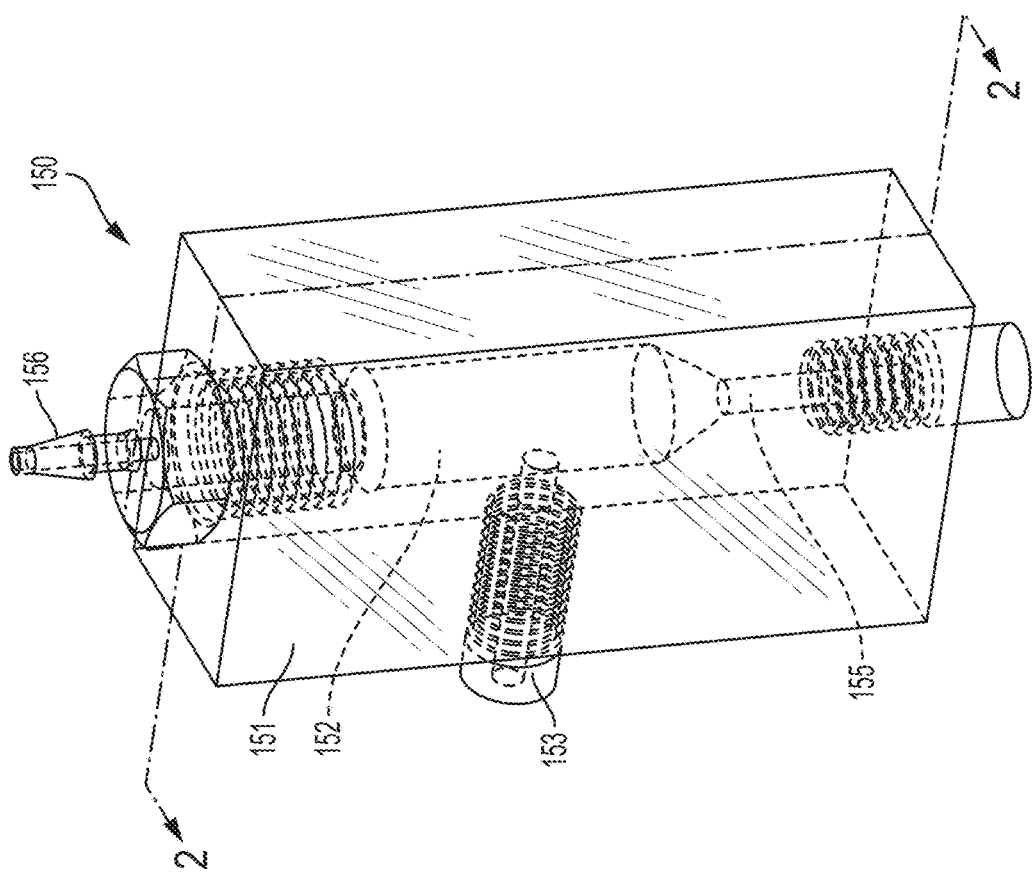
FIG. 5A shows an example bubble trap suitable for use in the systems shown in FIGS. 1 and 2.

FIGS. 5A and 5B show two views of a bubble trap 150 suitable for use in the systems shown in FIGS. 1 and 2. The bubble trap 150 includes features to prevent accumulation of fluid-borne particles, such as TILs, within the bubble trap 150. The bubble trap 150 is formed from a volume of material 151 with an internal cavity 152 into which liquid enters through an entry hole 153 and exits through an exit hole 155. By orienting the bubble trap 150 such that the entry hole 153 is elevated above the exit hole 155, gas bubbles entrapped in the liquid buoyantly rise toward the top of the cavity 152 and exit through a port 156, and are thereby separated from the fluid, which flows out of the bubble trap through the exit hole 155. In the cross-sectional view of FIG. 5A, FIG. 5B shows fluidic fittings 153a and 155a attached to the entry hole and exit hole, respectively, to facilitate connections to other fluid handling devices. In the portion of the cavity between the entry hole 153 and exit hole 155, all the interior walls of the cavity are steeply angled towards the exit hole 155, forming a tapered section 154, thereby guiding the flow of particles to the exit hole 155 and reducing entrapment of particles on the interior walls of the cavity 152.

In some implementations, the port 156 on the top of the bubble trap cavity 152 may be opened to release accumulated gases. In some other implementations, a gas-permeable membrane (not shown) covers an opening at the top of the cavity 152. A partial vacuum is created on the side of the membrane opposite to the cavity, thereby causing the extraction of gases through the membrane.

In some implementations, the bubble trap 150 is mechanically oscillated to dislodge particles within the cavity 152 and assist their movement toward the exit hole 155. The mechanical oscillation may be caused by an electromechanical transducer that is attached to the bubble trap 150, such as a motor with a mass eccentrically mounted on its shaft, a piezoelectric crystal subjected to an alternating current, or a voice coil.

In operation, the systems shown in FIGS. 1 and 2 can be used to test the efficacy of both chemotherapeutics as well as TIL based protocols in fighting tumors. In some implementations, tumor samples are collected using a 27 gauge needle by piercing the tumor and pulling a gentle vacuum on the syringe before removing the needle. Alternatively, larger tumor samples can be obtained and finely minced with a razor or scalpel. Then the fragments are sorted by size. In both methods, tumor fragments are selected for size by eye, stained en masse, and then selected more carefully for being the appropriate size, shape, and structure before being loaded into the device. The ideal fragment is compact, as wispy or filamentous projections can be a sign of cell death, and around 75-500 microns in diameter. The fragments from either method are generally not rounded. The syringe method yields more reproducible fragments with less variation in size and shape. The mincing method produces more fragments, but with more variation, and those fragments have to be more carefully selected When conducting assays using TILs, the TILs can be suspended with an appropriate medium for the TIL type. For example, for mouse cells, a Complete TIL medium can include:

Roswell Park memorial Institute medium ("RPMI") 1640 with L-Glutamine, no phenol red,
10% heat inactivated fetal bovine serum ("FBS"),
1% Penicillin-Streptomycin-Glutamine (100×),
10 mM 4-(2-hydroxyethyl)-1-piperazineethanesulfonic acid ("HEPES"),
100 uM 2-mercaptoethanol, and
200 U/mL recombinant mouse IL-2.

In some implementations, the TILs may be pre-treated with higher dose antibodies for about 18 hours, prior to being introduced into the primary pump reservoir, which can include a lower dose of the antibodies.

Monitoring of TIL-based assays can include real-time confocal imaging and assessment of tumor killing and TIL capture. Such analysis is enabled by staining of the tumors and TILs with agents to indicate death or specify identity. These agents include Annexin V for tumor death (or alternatives such as propidium iodide), CellTracker Green for tumor live stain, CellTracker Red for TILs, or Hoechst 33528 for TILs.

TIL isolation and removal is achieved by the use of mechanical and enzymatic digestion of the cells to single cells, magnetic sorting of the TIL populations with anti-CD45 coated beads, and expansion of the TIL population using anti-CD3/anti-C28 coated beads. As an example, use of the Miltenyi GentleMACS for automated tissue dissociation fits into this category. In some implementations, TIL populations may be modified with various cell transduction techniques, such as chimeric antigen receptor ("CAR")T cell therapy techniques to modify the genetics of the TILs, prior to the expansion of the TIL population and use in the assays.

For non-TIL-based operation, a single agent and multiplexed therapeutic agent testing for dose response with small molecule compounds can include exposure of the tumor to small molecules such as Erlotinib and Gefitinib, as well as therapeutic antibodies such as Trastuzumab, Keytruda, and Ipilimumab.

In some implementations, TILs can be introduced in combination with various chemotherapeutics to examine the effects of various combined therapies.

Certain experimental results using a system similar to that discussed above in relation to FIGS. 1-5 are discussed further below.

Figure 6:
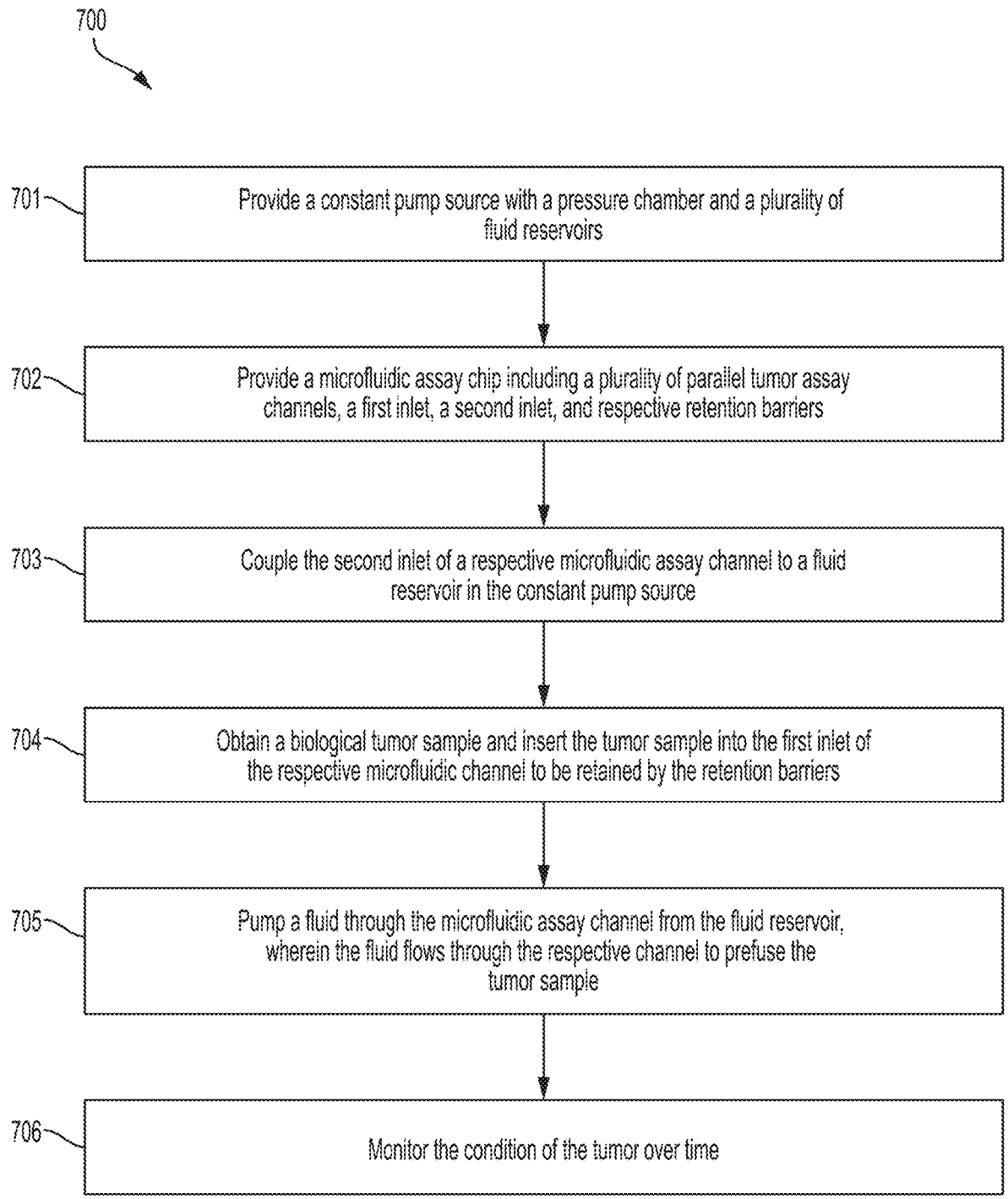
FIG. 6 illustrates a flowchart showing a non-limiting, exemplary method for analyzing a tumor sample in the presence of TILs using the disclosed microfluidic assay chip and constant pump source as shown in FIG. 1.

FIG. 6 illustrates a flowchart showing a non-limiting, exemplary method 700 for analyzing a tumor sample in the presence of TILs using the disclosed microfluidic assay chip 160 and constant pump source 110 as shown in FIG. 1. Method 700 includes providing a constant pressure pump 110 with a pressure chamber 130 and a plurality of fluid reservoirs 120 (step 701). Method 700 also includes providing a microfluidic assay chip 160, including a plurality of parallel tumor assay channels 180, wherein each channel includes a first inlet port 190a, a second inlet port 190b, and a retention barrier 200 (step 702). Next, the method 700 includes coupling the second inlet port 190b of a respective microfluidic assay channel 180 to a fluid reservoir 120 in the constant pump source 110 (step 703). Next, method 700 includes obtaining a biological tumor sample and inserting the tumor sample into the first inlet port 190a of the respective microfluidic channel 180 to be retained by the retention barrier 200 (step 704). The method 700 also includes pumping a fluid through the microfluidic assay channel from the fluid reservoir 120, wherein the fluid flows through the respective microfluidic channel 180 to perfuse the tumor sample (step 705). Next, method 700 includes monitoring the tumor over time (step 706).

First, method 700 includes providing a constant pressure pump 110 with a pressure chamber 130 and a plurality of fluid reservoirs 120 (step 701). In the constant pressure pump 110, fluid is located within the fluid reservoirs 120 installed in a sealed pressure chamber 130. The precise level of applied pressure, balanced against the hydraulic resistance of the flow circuit, drives the fluid through a tubing 140 that couples the microfluidic assay chip 160. In some implementations, the components of the pumping system can be designed and constructed to minimize drug sorption, avoid cytotoxicity or cell damage, and minimize sequestration or aggregation of cells in dead zones or other regions away from a tumor during device operation.

Method 700 also includes providing a microfluidic assay chip 160, including a plurality of parallel tumor assay channels 180, wherein each channel includes a first inlet port 190a, a second inlet port 190b, and a retention barrier 200 (step 702). The first inlet port 190a is used for initial introduction of a tumor sample, whereas the second inlet port 190b is used for introducing fluid from the fluid reservoirs in the constant pump source 110 to the respective microfluidic channel 180. The tumor sample may be introduced into the first inlet port 190a via a syringe or a fine needle biopsy. In some implementations, a total of twelves parallel and independent channels may be arranged on a glass-slide chip that measures about 95 mm wide by 35 mm in length. In some implementations, the microfluidic assay chip 160 may contain less than twelve channels. In other implementations, the microfluidic assay chip 160 may contain more than twelve channels. In microfluidic assay chips with six channels, the glass-slide chip can measure about 47.5 mm by 35 mm in length. In microfluidic assay chips with eighteen channels, the glass-slide chip can measure about 142.5 mm by 35 mm in length. The retention barrier 200 is configured to trap the tumor sample within the channel and allow fluid to perfuse the tumor sample. In some implementations, the retention barriers of each respective microfluidic assay channel may include between three to ten free-standing posts extending from the floor of the channel substantially to the top of the channel with at least one embedded post extending out from a channel sidewall to create a concave retaining barrier. In some implementations, the posts that make up the retention barrier 200 may be spaced apart from one another to have a lateral separation across the channel of about 20 μm to 40 μm. In some implementations, the shortest distance between any two adjacent posts is about 65 μm to 85 μm. In some implementations, the outermost free standing post of the plurality of posts is about between about 65 μm to 85 μm away from a nearest sidewall. The post pattern is designed to trap tumor fragments with a size range of interest and to accept variation in fragment size and shape without permitting fragments to slip through the posts or to be shredded by excessive flow through the gaps between the posts. The height of the channel may be varied to accommodate tumor fragments while balancing perfusion through and around the fragment.

Next, method 700 includes coupling the second inlet of a respective microfluidic assay channel 180 in the microfluidic assay chip 160 to a fluid reservoir 120 in the constant pump source 110 (step 703). The coupling of step 703 can be accomplished through a tubing 140. In some implementations, the tubing 140 is composed of polytetrafluorethylene or polyetheretherketone. The pressurized media flows out of the pressure chamber through the tubing 140, wherein an open end of the tube is submerged in the fluid reservoir. The other end of the tubing 140 couples to the second inlet port of a respective microfluidic channel 180. In some implementations, each tube 140 may be about 91.5 cm long with an inner diameter of about 304.8 μm. In some implementations, the tubing 140 from multiple reservoirs may be wrapped and ganged together to organize and streamline the fluidic assembly.

The tubing 140 is also connected to one or more bubble traps 150 located between the constant pressure pump 110 and the microfluidic assay chip 160. The bubble traps 150 remove gas bubbles from the fluid flowing through the tubing 140, wherein the fluid enters through a port on the side of each bubble trap and exists through the bottom, causing bubbles to buoyantly rise and become trapped at the tops of the cavities, where a venting port allows for removal of excess gas as needed. The bottom of each cavity is given a conical shape to funnel media and cells towards the exit port.

A resistive tubing 145 couples an outlet port of the each respective microfluidic assay channel 180 to a waste receptacle 170. In some implementations, the resistive tubing 145 is made from polyether ether ketone (PEEK) tubes. The resistance, R, of the tubing may be computed by the following equation:

$$R = \frac{8 * v * \iota}{\pi * \frac{d^4}{2}}$$

Where d is the inner diameter of the resistive tubing, $\iota$ is the length of the resistive tubing, and v is the fluid viscosity. In some implementations, the inner diameter of the PEEK tubes may be 127 μm with a length of about 115 cm.

In some implementations, the waste receptacle may be a common waste receptacle, wherein the fluid from each channel's outlet port accumulates in the common waste receptacle. In other implementations, each respective microfluidic channel may have its own respective waste receptacle 170. In some implementations, the resistive tubing may couple the outlet port of each respective microfluidic channel 180 to a second recirculating pump 111, as shown in FIG. 2.

Next, method 700 includes obtaining a biological tumor sample and inserting the tumor sample into the first inlet port of the respective microfluidic channel 180 to be retained by the retention barrier 200 therein (step 704). In some implementations, the tumor sample is harvested at a size of about 80-120 mm³ and dissected into smaller fragments about 1 mm³. In some implementations, tumor fragments may be loaded into the microfluidic device by collecting the tumor fragments into a capillary tube of a micropipette and injecting the fragments into the first inlet port 190a of microfluidic channel 180. In other implementations, tumor fragments may be loaded into the microfluidic device by using a fine needle biopsy. In some implementations, tumor fragments may be guided into the retention barrier by gently pushing fluid through the first inlet port 190a with a blunt-tipped syringe.

The method 700 also includes pumping a fluid through the microfluidic assay channel from the fluid reservoir in the constant pressure pump, wherein the fluid flows through the respective channel to perfuse the tumor sample (step 705). The fluid can represent a particular experimental condition. In some implementations, the fluid is media only. In some implementations, the fluid includes untreated TILs in media. In some implementations, the fluid includes TILs treated with various agents in media. In an example implementation, the fluid may contain phenol red free RPMI with 1% penicillin/streptomycin, 10% heat inactivated FBS, 100 um 2-Mercaptoethanol, 10 mM HEPES buffer, and fluorescent labeled Annexin V protein.

The fluid can be flowed at a rate of about 1 μL/min, depending upon the channel dimensions, but is generally in the range of 0.5 to 5.0 μL/min.

Next, method 700 includes monitoring the tumor over time (step 706). The visual analysis of the tumor sample determines the efficacy of the TILs or other drugs flowing through the device. In some implementations, the monitoring device may be a confocal microscope positioned above the microfluidic assay channels.

The systems and methods disclosed herein can be used as a personalized therapy whereby tumor cells/tissue from individual patients can be tested for the most effective drug/drug combinations or personalized tumor microenvironment pharmacokinetic studies. The systems and methods disclosed herein may be used to diagnose, treat and manage include, but are not limited to, cancer, diabetes, inflammatory conditions, and patients with graft versus host disease. The systems and methods can be used for drug development and drug testing for efficacy; biomarker discovery and validation in microfluidics; and toxicology assays using liver and other non-tumoral tissue fragments.

Experimental Results

The following examples are provided to more fully illustrate various implementations of the present technology. These examples should in no way be construed as limiting the scope of the invention.

The current systems and methods disclosed herein can be used to monitor the impact of TILs on tumor cells. For example, the microchannel fluidic assay device described above in relation to FIG. 1 was used to investigate the response of mouse colon adenocarcinoma cells (MC38) to TILs in order to identify the TILs' effect on cell death and tumor shrinkage. First, the system was prepared by washing all tubing and connectors with 10% Terg-a-zyme solution (Sigma Z273287) and rinsed thoroughly with water before autoclaving for sterilization. Microfluidic devices and acrylic bubble traps were sterilized in EtO gas and placed in a vacuum chamber for at least 48 hours before use. Complete microfluidic systems were assembled under sterile conditions in a bio-containment hood and primed by flowing 70% ethanol overnight. Ethanol was purged from the system by flowing distilled $H_2O$ for two hours followed by two hours of complete media flow.

Next, the MC38 tumors were harvested at a size of about 80-120 mm³ and dissected into smaller fragments of about 1 mm³. Then, TIL expansion was initiated by placing the tumor fragments into a complete medium consisting of RPMI 1640/Glutamax, 10% heat inactivated FBS, 55 μM 2-mercaptoethanol, 10 mM HEPES, 1% penicillin/streptomycin and 200 U/mL of rmIL-2. Next, the TIL medium is placed in the wells of a 24-well plate with ultra-low attachment surface, cultured in a 37° C. humidified incubator with 5% $CO_2$. After TILs migrated out of the fragments, half of the medium was replaced with a fresh complete medium. TILs started to expand following lysis of tumor cells. The culture was split when reaching 80% confluency. TILs were harvested following two weeks of culture when viability reached more than 80%, and cryopreserved in 90% FBS—10% dimethyl sulfoxide ("DMSO"). Co-culture of TILs with autologous or allogeneic tumor cells demonstrated that the expanded TILs reacted specifically to a tumor antigen by stimulating IFNγ secretion measured by Meso Scale Discovery ("MSD") electrochemiluminescence detection.

Next, the extracted tumor fragments were washed in PBS by centrifugation and stained with 20 μM Cell Tracker Green (Invitrogen C7025) in PBS for 1 hour at 4° C. Tumor fragments with strong viability indicated by bright Cell Tracker staining were hand-selected under a microscope using a micropipette and transferred to FBS. Then, the tumor fragments were loaded into the first inlet port of the microfluidic channel. To load tumor fragments into the microfluidic channel, single fragments were collected into the capillary tube of a micropipette and injected into the tubing of the device tumor introduction port. Tumor fragments were guided into the retention barrier by gently pushing media through the loading port with a blunt-tipped syringe. Complete media (phenol red free RPMI with 1% penicillin/streptomycin, 10% heat inactivated FBS, 100 μM 2-Mercaptoethanol, and 10 mM HEPES buffer) containing florescent labeled Annexin V protein (Thermo Fisher A35110) was then loaded into the fluid reservoirs and flowed through the system at approximately 1 μL/min overnight. Baseline tumor viability was measured by confocal microscopy.

Figure 7:
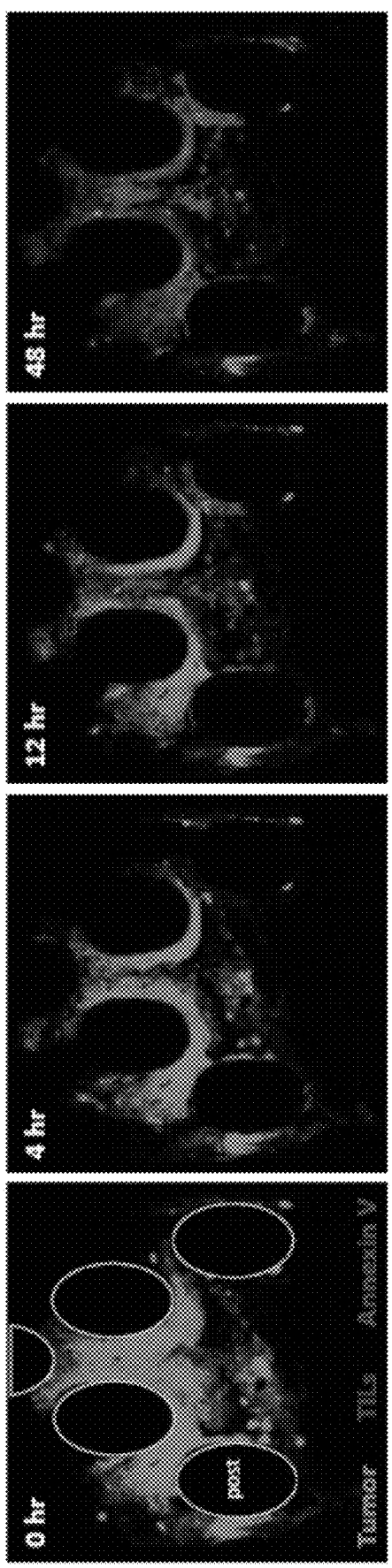
FIG. 7 illustrates central Z-stack images of an individual tumor sample at t=0, 4, 12, and 48 hours post introduction of TILs.

Next, the fluid reservoirs 120 containing the fluid TILs were placed in the pressure chamber 130 and placed on a magnetic stirrer and hot plate to continuously agitate the TILs. A temperature probe was also threaded through a port on the lid of the pressure chamber 130 and placed in the fluid reservoirs 120 at the level of the TILs to ensure that the temperature was 37° C. Fluid reservoirs 120 containing TILs as well as control fluid reservoirs 120 with no TILs were stirred constantly by the magnetic stirrers at a low rate to prevent clumping and settling. Next, pressure from the constant pressure pump 110 caused the TIL fluid to flow from the fluid reservoirs 120 to a respective microfluidic channel 180, where the fluid perfused the tumor sample trapped in the retention barrier 200. FIG. 7 illustrates central Z-stack images of an individual tumor sample at t=0, 4, 12, and 48 hours post introduction of TILs in real-time monitoring. In the image green areas indicate live tumor cells, blue areas indicate TILs, and red areas indicate annexin V or cell apoptosis. In FIG. 7 at t=48 hours the tumor volume appears to decrease over time in the presence of TILs. The image also an increase in apoptosis. Thus, the system and methods of the current disclosure can be used to measure the real-time viability and interactions between tumor samples and TILs over the course of several days.

Figure 8A:
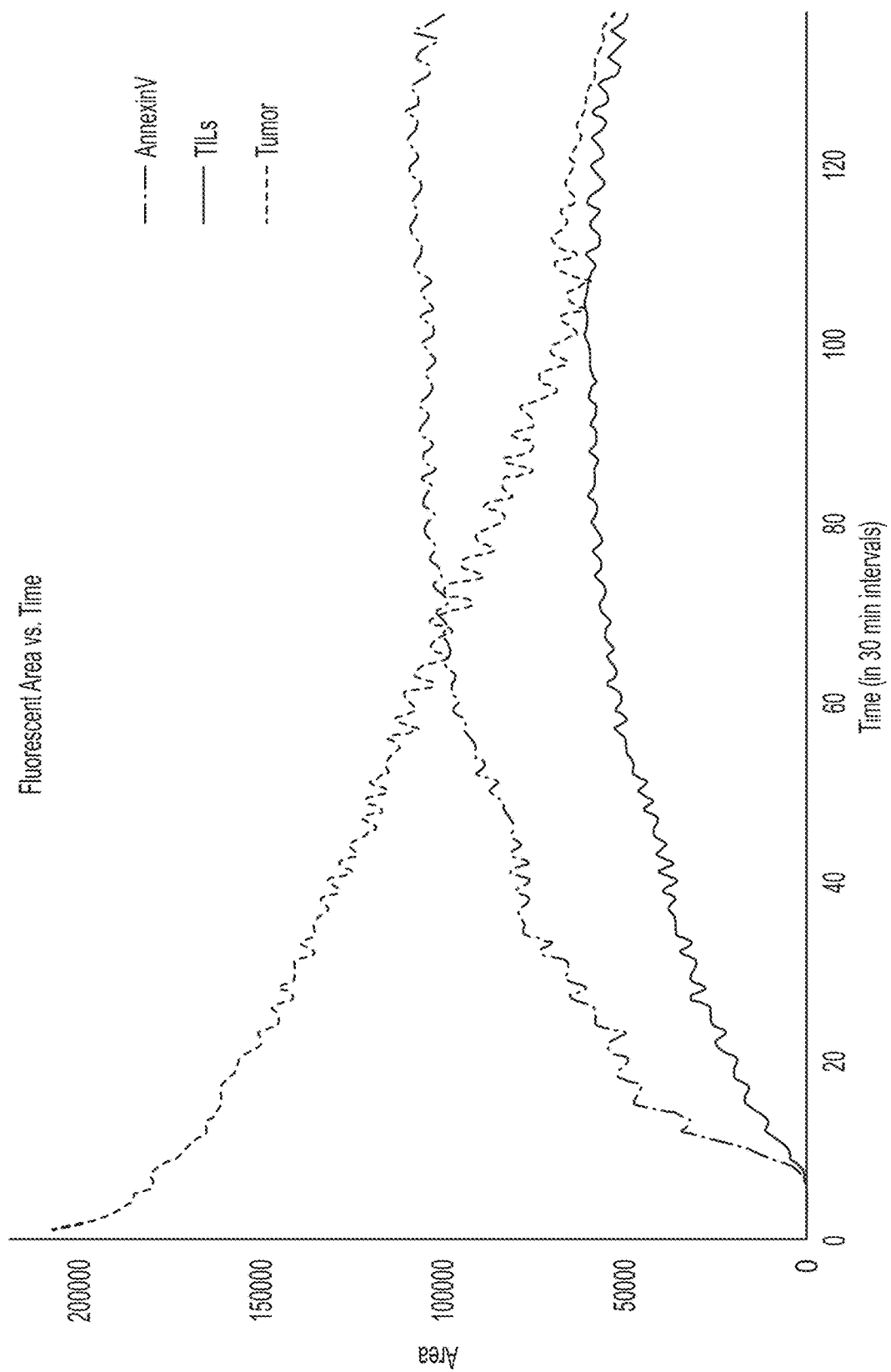
FIG. 8A illustrates the effectiveness of TIL treatments on a tumor sample in the single pass device configuration of FIG. 1.
Figure 8B:
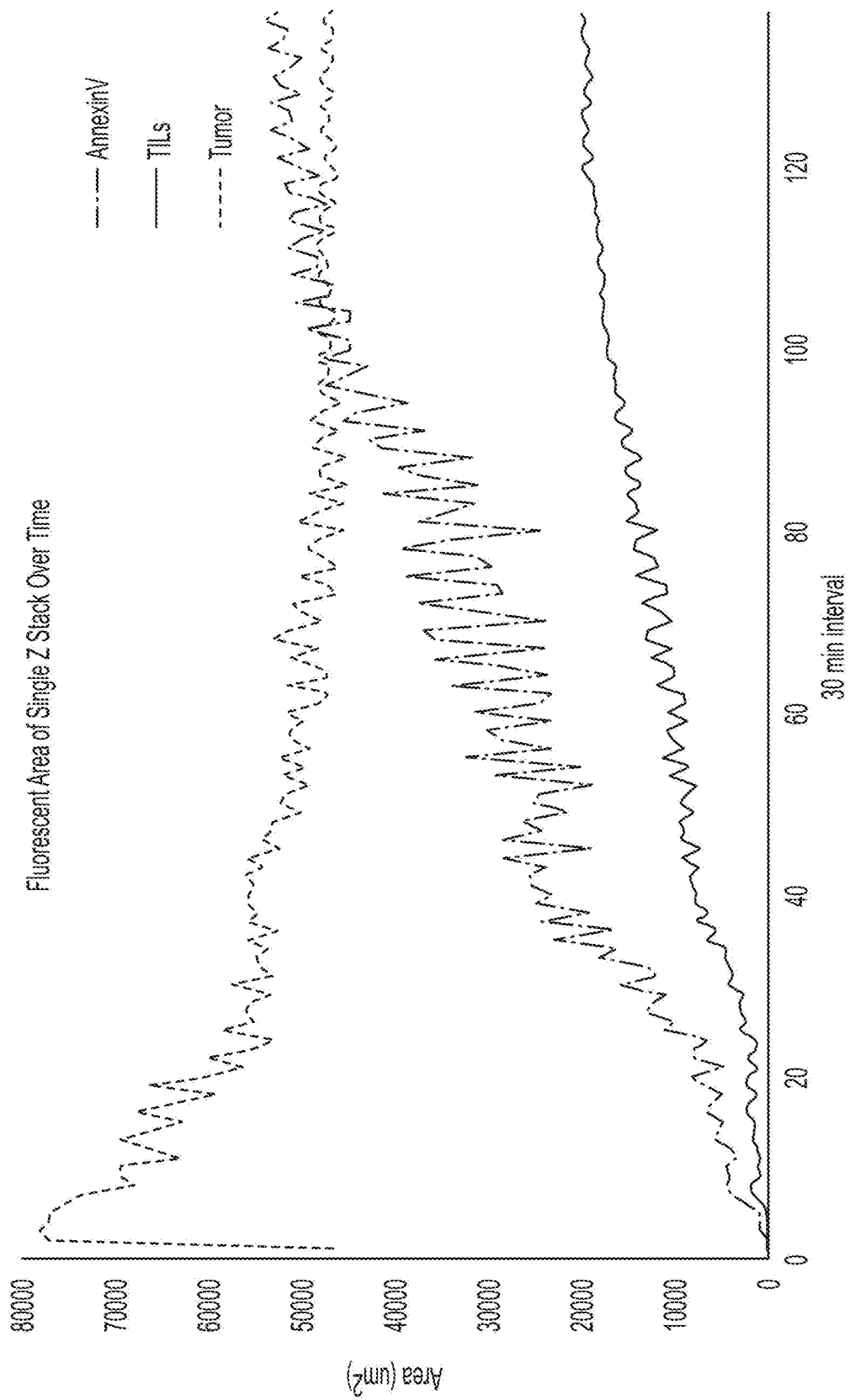
FIG. 8B illustrates the effectiveness of TIL treatments on a tumor sample in the single pass device configuration of FIG. 1.
Figure 8C:
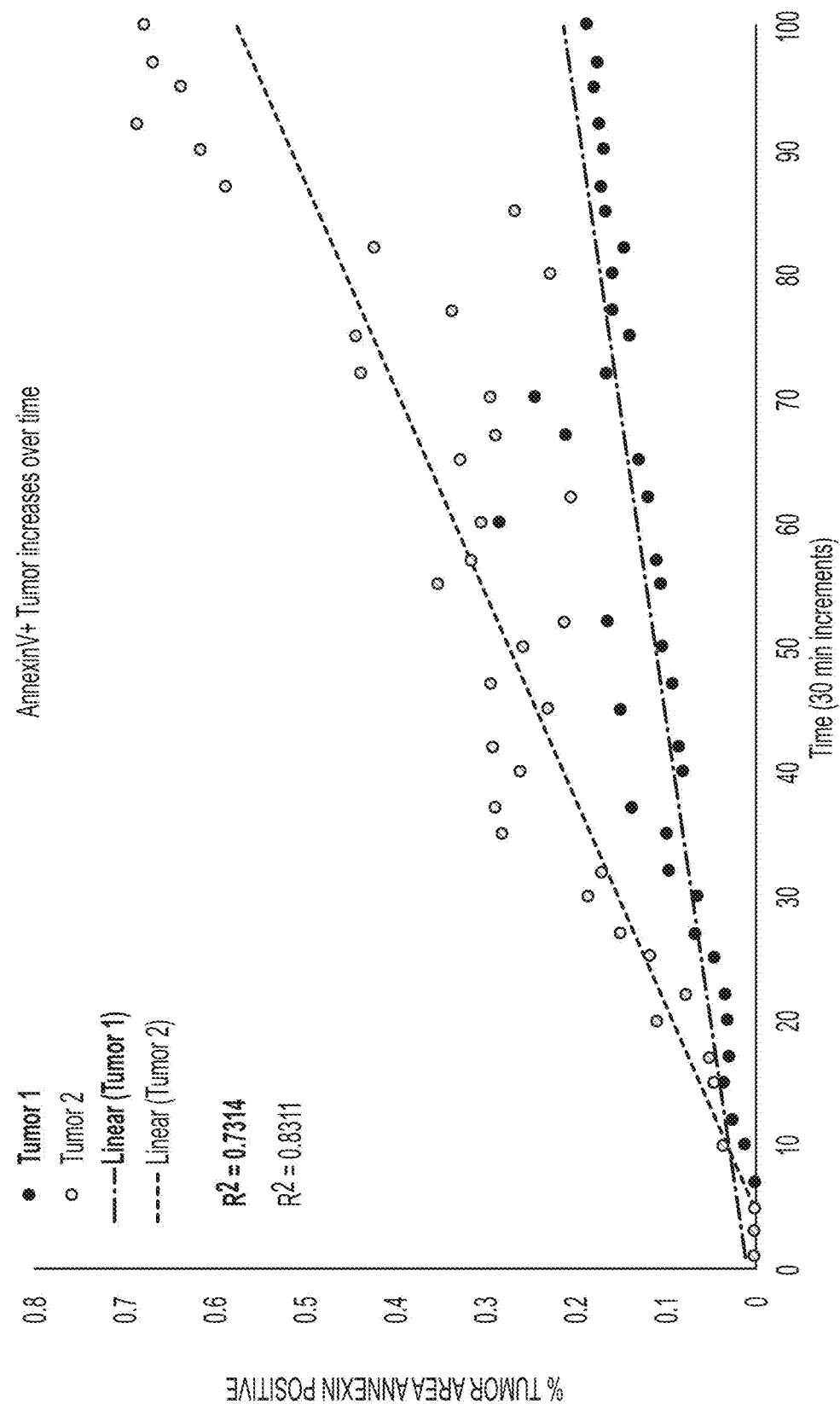
FIG. 8C illustrates the percentage of annexin-positive tumor over time.

In another example using the single pass configuration of FIG. 1 and the methods of FIG. 6, the effectiveness of TIL treatments on tumor samples were measured in real time. First, tumor fragments were stained with cell tracker green (10 μM CMFDA) and introduced into 5 channels of the device in FIG. 1. After 24 hours, TILs were stained with 5 μM cell tracker red and suspended at 1×10$^5$ cells/mL in complete TIL medium with 200 U/mL interleukin 2 (IL-2) and 1:2000 dilution annexin V-AF555. About 2.4×10$^6$ live cells at 74% viability were contained and a stir bar kept the cells suspended in the TIL fluid reservoir. Next, TILs were flowed through the device and images were taken every 30 min, starting at the time the TILs started flowing, up to 2.5 days. The pump was set to a pressure routinely demonstrated to provide a flow rate of about 1 μl/mL and flow sensors were disconnected to prevent clogging. FIG. 8A shows the results of a tumor sample #1 and FIG. 8B shows the results of a tumor sample #2, wherein green line indicates live staining of tumor, the red line indicates annexin V stain, and the blue line indicates live staining of TILs. In both experiments, the percentage of annexin-positive cells increased with time, indicating that tumor-cell apoptosis was being mediated by TILs, as shown in FIG. 8C. Similarly, FIGS. 8A and 8B show a decrease of tumor cell area as apoptosis occurs. The results of the experiment show that tumor volume appears to decrease over time in the presence of T cells and the percentage of annexin V-positive tumor cells increases over time.

Figure 9:
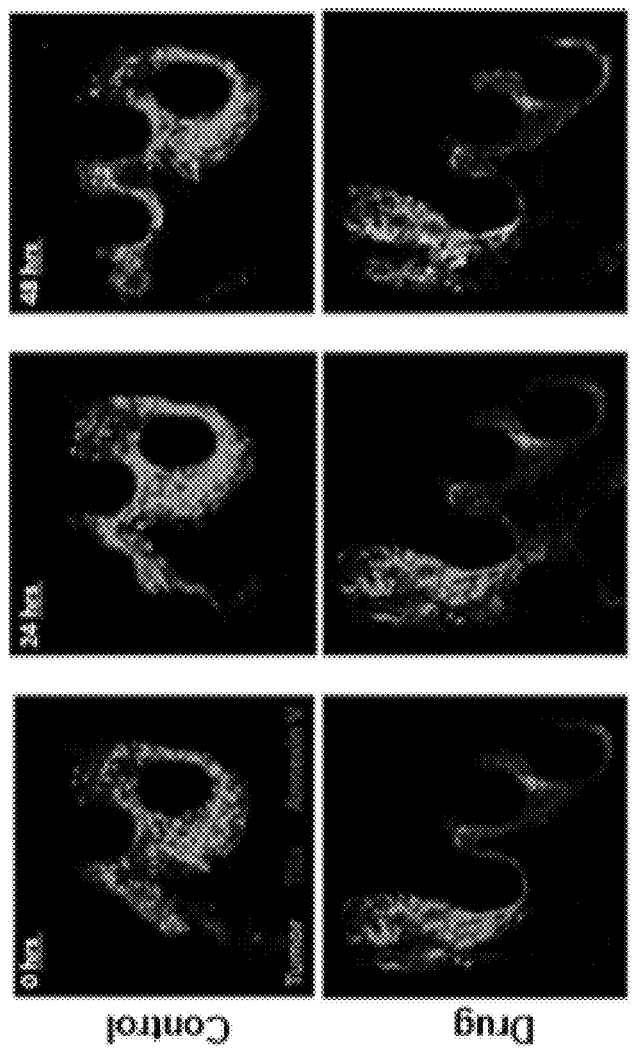
FIG. 9 shows the daily confocal imaging and custom image analytics evaluating the changes in tumor death overtime using TILs and anti-PD-1 antibody.

In another example, the microchannel fluidic assay device can be used to investigate the response of a tumor sample to an anti-PD-1 antibody. Six MC38 tumor samples were studied in six separate microfluidic channels. Two samples remained controls with no TILs present, two samples were treated with IgG, and two samples were treated with TILs pretreated with 100 μg/mL of anti-PD-1 antibody overnight prior to treatment. Similar to step 704, next, the six tumors samples were loaded into the first inlet port 190a of each respective microfluidic channel 180 with media-only fluid flowed through the constant pump source and the microfluidic assay channel overnight. Then, similar to step 705 the constant pressure pump flowed TILs from two fluid reservoirs to the microfluidic channels at 100K cells/mL for 24 hours. Similarly, the tumor samples treated as controls and treated with IgG were also perfused with a constant flow from the constant pressure pump 110 and their respective fluid reservoirs 120. After 24 and 48 hours of treatment, media vials were refilled without adding more TILs or anti-PD-1 antibody. A flow sensor was set in the pump system to measure media outflow and to monitor a flow rate-target of 1 μl/min with general range between 1 and 2 μl/min. FIG. 9 shows the daily confocal imaging and custom image analytics evaluating the changes in tumor death overtime using TILs and anti-PD-1 antibody. In FIG. 9, the images show screen capture at t=0, 24 and 48 hours after the start of the experiment at the same selected slice within the high-resolution confocal microscope z-stack for isotype-control-treated (top) and anti-PD-1 antibody treated (bottom) TILs. The green areas indicate tumor cells, blue areas indicate TILs, the red areas indicate annexin V stained (apoptotic) cells, and yellow areas indicates debris. The MC38 tumor sample treated with TILs pre-treated with anti-PD-1 antibody show a significant increase in apoptotic (red stained) cells, indicating cell death, as compared to the non-TIL treated control conditions. Thus, the system and method of the present disclosure demonstrate an in vivo condition that permits screening and testing of labile drug candidates and the susceptibility of a tumor specimen to treatment.

Figure 10:
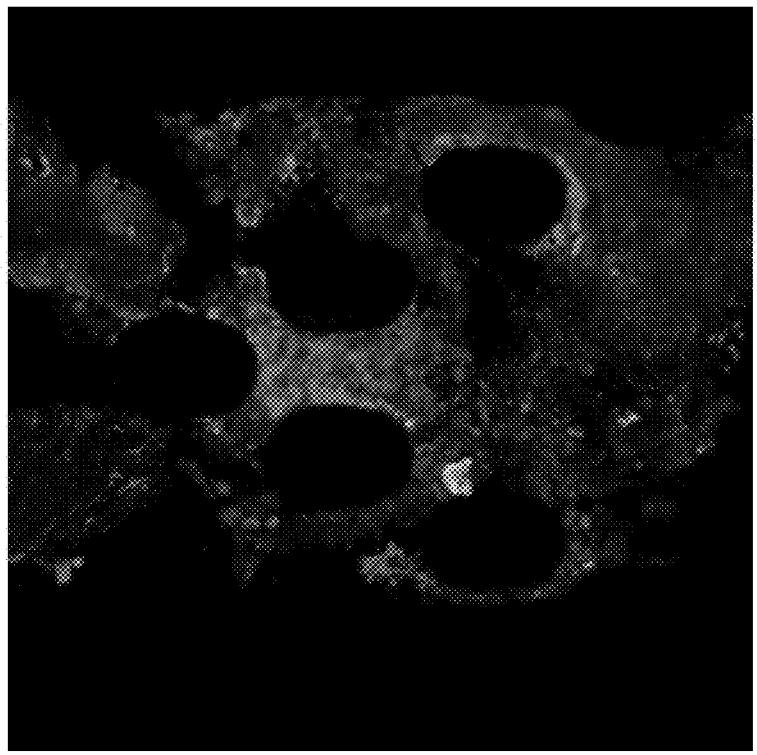
FIG. 10 shows an image of a human Non-Small-Cell Lung Cancer tumor after 24 hours of perfusion in the presence of TILs treated with isotype control antibody and anti-PD-1 antibody.
Figure 10:
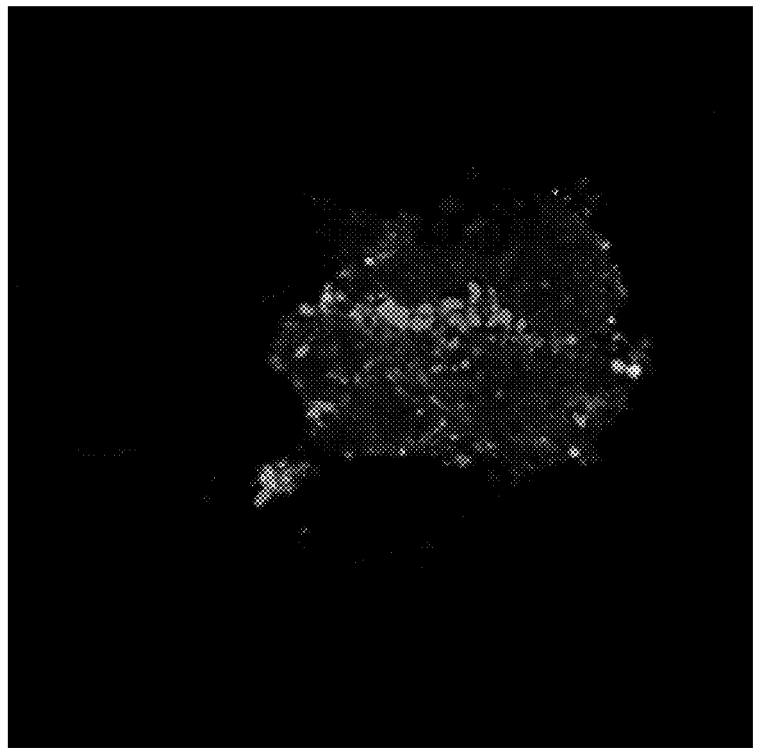

In another example, the system and methods described herein were used to investigate the TIL response on a human tumor sample. First, the human tissue sample was fragmented and inserted into respective channels similar to step 704 in FIG. 6. Then, fluid containing extracted TILs was pumped through the microfluidic assay channel from the fluid reservoirs in the constant pump source, similar to step 705 above. FIG. 10 shows an image of a human Non-Small-Cell Lung Cancer ("NSCLC") tumor after 24 hours of perfusion in the presence of TILs treated with isotype control antibody (left) and anti-PD-1 antibody (right). The green areas indicate tumor cells, blue areas indicate TILs, the red areas indicate annexin V stained (apoptotic) cells, and yellow areas indicates debris. At 24 hours post TIL administration, the NSCLC tumor fragment treated with the anti-PD-1 antibody displayed substantial TIL infiltration with proximal cellular apoptosis as indicated by positive annexin-V staining. TILs infiltrated the tumors as circumscribed, aggregate fronts, as opposed to well-resolved, diffuse cellular infiltration.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

What is claimed is:

1. A method of evaluating the efficacy of tumor infiltrating lymphocytes (TILs) on tumor samples, comprising:
providing a microfluidic assay chip and a suspension maintaining pump, and a plurality of fluid reservoirs, wherein the fluid reservoirs are configured to hold a volume of fluid and TILs suspended within the fluid and are fluidically coupled to the microfluidic assay chip by tubing, the microfluidic assay chip including:
a plurality of parallel assay channels, each parallel assay channel including:
a first inlet at a proximal end of the assay channel for introduction of a tumor sample into the microfluidic assay chip;
a second inlet at the proximal end of the assay channel coupling a fluid reservoir to the assay channel, wherein the coupling comprises a connection via a portion of the tubing, wherein the second inlet has a smaller diameter than the first inlet;
a retention barrier located within the assay channel and configured to trap a tumor sample such that the fluid and TILs perfuse through the tumor sample; and
an outlet at a distal end of the assay channel configured to allow fluid and TILs to flow out of the microfluidic assay chip, wherein,
introducing tumor samples to the array of parallel assay channels via the first inlets of the respective assay channels;
retaining the tumor samples in the respective assay channels via respective retention barriers;
flowing fluid and TILs suspended within the fluid from the fluid reservoirs located in the suspension maintaining pump into the proximal ends of the respective assay channels via the respective second inlets such that the fluid and TILs flow through the respective channels, thereby inducing interstitial flow of the fluid and TILs through the tumor samples such that the fluid and TILs perfuse through the tumor samples;
collecting the fluid and TILs at the outlets at the distal ends of the assay channels; and
monitoring the condition of the tumor samples over time during the flowing of the fluid and TILs.

2. The method of claim 1, wherein the tumor samples comprises portions of animal or human tumors or engineered tumor spheroids.

3. The method of claim 1, wherein the suspension maintaining pump comprises a stirred peristaltic pump.

4. The method of claim 3, wherein the suspension maintaining pump comprises a constant pressure source.

5. The method of claim 1, further comprising removing bubbles from the fluid prior to its introduction into the respective assay channels with a plurality of bubble traps located between the fluid reservoirs and the microfluidic assay chip, each bubble trap having an exit port located below an entry port configured to remove gas bubbles from the fluid.

6. The method of claim 1, comprising routing the fluid through resistive tubing from the outlet of each assay channel to a waste receptacle.

7. The method of claim 1, comprising routing the fluid through resistive tubing from the outlet of each assay channel to a recirculating pump for pumping fluid flowed through the microfluidic assay chip back to respective reservoirs.

8. The method of claim 6, comprising removing cells from the fluid before the fluid enters the waste receptacle with a plurality of particulate traps located between the microfluidic assay chip and the waste receptacle.

9. The method of claim 1, wherein the suspension maintaining pump comprises a stirrer rod and a magnetic or electromagnetic plate configured to oscillate, wherein the oscillation of the plate causes motion of the respective stirrer rods within the reservoirs, thereby maintaining suspension of the TILs in the fluid within the reservoirs.

10. The method of claim 1, wherein the retention barrier comprises a plurality of posts extending from the bottom of the channel to the top of the channel.

11. The method of claim 2, wherein the tumor sample is between 75 and 500 microns in diameter.

12. The method of claim 1, further comprising monitoring the tumor samples located within the retention barriers with an imaging device.

* * * * *